(12) United States Patent
Bentwich et al.

(10) Patent No.: US 8,481,506 B2
(45) Date of Patent: Jul. 9, 2013

(54) NUCLEIC ACIDS INVOLVED IN VIRAL INFECTION

(75) Inventors: Issac Bentwich, DN Misgav (IL); Amir Avniel, Tel-Aviv (IL); Ranit Aharonov, Tel-Aviv (IL); Yael Karov, Tel-Aviv (IL); Yonat Shemer-Avni, Beer Sheva (IL); Asal Levy, Nes-Ziona (IL)

(73) Assignee: Rosetta Genomics, Ltd., Rehovot (IL)

( * ) Notice: Subject to any disclaimer, the term of this patent is extended or adjusted under 35 U.S.C. 154(b) by 683 days.

(21) Appl. No.: 12/517,760

(22) PCT Filed: Dec. 5, 2007

(86) PCT No.: PCT/IB2007/004718
§ 371 (c)(1),
(2), (4) Date: Apr. 5, 2010

(87) PCT Pub. No.: WO2009/024834
PCT Pub. Date: Feb. 26, 2009

(65) Prior Publication Data
US 2010/0184205 A1   Jul. 22, 2010

Related U.S. Application Data

(60) Provisional application No. 60/868,666, filed on Dec. 5, 2006, provisional application No. 60/971,265, filed on Sep. 11, 2007.

(51) Int. Cl.
*C12N 15/11* (2006.01)
*A61K 48/00* (2006.01)
*C07H 21/02* (2006.01)
*C07H 21/04* (2006.01)

(52) U.S. Cl.
USPC .......................... 514/44 A; 536/24.5

(58) Field of Classification Search
USPC ............................. 514/44; 536/24.5
See application file for complete search history.

(56) References Cited

U.S. PATENT DOCUMENTS

| | | |
|---|---|---|
| 5,034,506 A | 7/1991 | Summerton et al. |
| 5,124,246 A | 6/1992 | Urdea et al. |
| 5,235,033 A | 8/1993 | Summerton et al. |
| 5,359,100 A | 10/1994 | Urdea et al. |
| 5,545,730 A | 8/1996 | Urdea et al. |
| 5,571,670 A | 11/1996 | Urdea et al. |
| 5,580,731 A | 12/1996 | Chang et al. |

(Continued)

FOREIGN PATENT DOCUMENTS

| | | |
|---|---|---|
| WO | WO 93/23569 A1 | 11/1993 |
| WO | WO 94/02595 A1 | 2/1994 |

(Continued)

OTHER PUBLICATIONS

Bartel et al., "MicroRNAs: At the Root of Plant Development?", Plant Physiology, Jun. 2003, vol. 132, pp. 709-717.

(Continued)

*Primary Examiner* — Terra Cotta Gibbs
(74) *Attorney, Agent, or Firm* — Polsinelli PC; Teddy C. Scott, Jr.; Ron Galant

(57) ABSTRACT

Provided herein are isolated viral and human nucleic acids associated with viral infection and various nucleic acid molecules relating thereto or derived therefrom. The nucleic acids may be useful for the prevention, treatment and diagnosis of viral infections.

10 Claims, 8 Drawing Sheets

U.S. PATENT DOCUMENTS

| | | | |
|---|---|---|---|
| 5,591,554 | A | 1/1997 | Chang et al. |
| 5,594,117 | A | 1/1997 | Urdea et al. |
| 5,594,118 | A | 1/1997 | Urdea et al. |
| 5,597,909 | A | 1/1997 | Urdea et al. |
| 5,624,802 | A | 4/1997 | Urdea et al. |
| 5,635,352 | A | 6/1997 | Urdea et al. |
| 5,681,697 | A | 10/1997 | Urdea et al. |
| 5,681,702 | A | 10/1997 | Collins et al. |
| 6,506,559 | B1 | 1/2003 | Fire et al. |
| 6,573,099 | B2 | 6/2003 | Graham |
| 7,687,616 | B1 | 3/2010 | Bentwich et al. |
| 2002/0115080 | A1 | 8/2002 | Skouv et al. |
| 2004/0033978 | A1 | 2/2004 | Anderson et al. |
| 2005/0107325 | A1 | 5/2005 | Manoharan et al. |
| 2005/0182005 | A1 | 8/2005 | Tuschl et al. |
| 2005/0261218 | A1* | 11/2005 | Esau et al. .................. 514/44 |
| 2006/0142228 | A1 | 6/2006 | Ford et al. |
| 2006/0257851 | A1 | 11/2006 | Bentwich |
| 2007/0042380 | A1 | 2/2007 | Bentwich et al. |

FOREIGN PATENT DOCUMENTS

| | | |
|---|---|---|
| WO | WO 99/04819 A1 | 2/1999 |
| WO | WO 99/05094 A1 | 2/1999 |
| WO | 2005/116250 A2 | 12/2005 |
| WO | 2006/110762 A2 | 10/2006 |

OTHER PUBLICATIONS

Bartel et al., "MicroRNAs: Genomics, Biogenesis, Mechanism and Function", Cell, Jan. 23, 2004, vol. 116, pp. 281-297.

Brennecke et al. "Principles of MicroRNA-Target Recognition", PLoS Biology, March, 205, vol. 3, Issue 3, pp. 1-15.

Cheng et al., "Antisense inhibition of human miRNAs and indications for an involvement of miRNA in cell growth and apoptosis", Nucleic Acids Research, 2005, vol. 33, No. 4, pp. 1290-1297.

Doench et al. "Specificity of microRNA target selection in translational repression", Genes & Development, 2004, pp. 1-8.

Esau et al., "MicroRNA-143 Regulates Adipocyte Differentiation", Journal of Biological Chemistry, Dec. 10, 2004, vol. 279, No. 50, pp. 52361-52365.

Hofacker et al., "Fast Folding and Comparison of RNA Secondary Structures", Chemical Monthly, 1994, vol. 125, pp. 167-188.

Krek et al., "Combinatorial microRNA target predictions", Nature Genetics, Apr. 2003, pp. 1-6.

Krutzfeldt et al., "Silencing of microRNAs in vivo with 'antagomirs'", Nature, 2005, vol. 430, pp. 1-5.

Lewis et al., "Conserved Seed Pairing, Often Flanked by Adenosines, Indicates that Thousands of Human Genes are MicroRNA Targets", Cell, Jan. 14, 2005, vol. 120, pp. 15-20.

Lim et al., "Microarray analysis shows that some microRNAs downregulate large numbers of target mRNAs", Nature, 2005, pp. 1-6.

Pruitt et al., "NCBI Reference Sequence (RefSeq): a curated non-redundant sequence database of genomes, transcripts and proteins", Nucleic Acids Research, 2005, vol. 33, pp. D501-504.

Shi et al., "Facile means for quanitfying microRNA expression by real-time PCR", BioTechniques, Oct. 2005, vol. 39, No. 4, pp. 519-524.

Soutschek et al., "Therapeutic silencing of an endogenous gene by systemic administration of modified siRNAs", Nature, Nov. 11, 2004, vol. 432, pp. 173-178.

Tatusova et al., "Complete genomes in WWW Entrez: data representation and analysis", Bioinformatics, 1999vol. 15, Nos. 7-8, pp. 536-543.

Yetka et al., "MicroRNA-Directed Cleavage of HOXBB mRNA", Science, Apr. 23, 2004, vol. 304, pp. 594-596.

International Search Report, PCT/US08/52086.

GenBank-FB989997. Sequence 2015 from Patent W02005116250. Accession No. FB989997. Posting date: Jan. 23, 2009, [online]. [Retrieved on Oct. 14, 2011. Retrieved from the Internet: <URL: http://www.ncbi.nlm.nih.gov/nuccore/FB989997> Journal Patent: WO 2005116250-A2 . . . Dec. 8, 2005. nucleotide sequence that is 100% identical to the claimed Seq ID No. 15.376.

GenBank_FB989191. Sequence 1209 from Patent W02005116250, Jun. 29, 2009 [online]. [Retrieved on Jul. 21, 2011]. Retrieved from the Internet: <URL:http://www.ncbi.nlm.nih.gov/nuccore/FB989191> Journal Patent: WO 2005116250- A2 . . . Dec. 8, 2005. Sequence, 100% identical to the claimed for Seq ID No. 1.

* cited by examiner

NUCLEIC ACIDS INVOLVED IN VIRAL INFECTION

CROSS REFERENCE TO RELATED APPLICATIONS

This is the national stage of International Application No. PCT/IB07/04718, filed on Dec. 5, 2007 which claims the benefit of U.S. Provisional App. No. 60/868,666, filed Dec. 5, 2006 and U.S. Provisional App. No. 60/971,265, filed Sep. 11, 2007, the contents of all of which are incorporated herein by reference.

FIELD OF THE INVENTION

Described herein are viral and host microRNA molecules associated with viral infections, as well as various nucleic acid molecules relating thereto or derived therefrom.

BACKGROUND OF THE INVENTION

MicroRNAs (miRNAs) are a family of 18-24 nucleotide long non-coding small RNAs, that suppress translation of target genes by binding to their mRNA, thereby regulating the expression of at least 30% of all human genes. Although miRNAs are present in a wide range of species including *C. elegans, Drosophila* and humans, they have only recently been identified. More importantly, the role of miRNAs in the development and progression of disease has only recently become appreciated. There are currently about 500 known human microRNAs, and their number probably exceeds 800.

As a result of their small size, miRNAs have been difficult to identify using standard methodologies. A limited number of miRNAs have been identified by extracting large quantities of RNA. miRNAs have been identified that contribute to the presentation of visibly discernable phenotypes. Expression array data show that miRNAs are expressed in different developmental stages or in different tissues. The restriction of miRNAs to certain tissues or at limited developmental stages indicates that the miRNAs identified to date are likely only a small fraction of the total miRNAs.

Computational approaches have recently been developed to identify the remainder of miRNAs in the genome. Tools such as MiRscan and MiRseeker have identified miRNAs that were later experimentally confirmed. Based on the fundamental importance of miRNAs in mammalian biology and disease, the art needs to identify unknown miRNAs.

Viruses can establish a variety of types of infection. These infections can be generally classified as lytic or persistent, though some lytic infections are considered persistent. Generally, persistent infections fall into two categories: (1) chronic (productive) infection, i.e., infection wherein infectious virus is present and can be recovered by traditional biological methods and (2) latent infection, i.e., infection wherein viral genome is present in the cell but infectious virus is generally not produced except during intermittent episodes of reactivation. Persistence generally involves stages of both productive and latent infection.

Lytic infections can also persist under conditions where only a small fraction of the total cells are infected (smoldering (cycling) infection). The few infected cells release virus and are killed, but the progeny virus again only infect a small number of the total cells.

Traditional treatments for viral infection include pharmaceuticals aimed at specific virus derived proteins, or recombinant (cloned) immune modulators (host derived), such as the interferons. However, the current methods have several limitations and drawbacks which include high rates of viral mutations which render anti-viral pharmaceuticals ineffective. For immune modulators, limited effectiveness, limiting side effects, a lack of specificity all limit the general applicability of these agents. Also the rate of success with current antivirals and immune-modulators has been disappointing.

Viral infections are a continuing medical problem because, like any rapidly-dividing infectious agent, there are continuing mutations that help some sub-populations of viruses continue to be resistant to current treatment regimens. Many virally-based diseases do not have effective anti-viral treatments, because such treatments address the symptoms of the viral disease and not the root cause of the disease. There is a need in the art to discover and develop new anti-viral therapies.

SUMMARY OF THE INVENTION

Provided herein are compositions and methods for the identification, suppression and modulation of viral infection in a target cell. Also provided are pharmaceutical compositions and kits for use in practicing the methods. The compositions and methods may be used in a variety of applications, including the treatment of subjects suffering from a viral mediated disease condition.

Also provided is an isolated nucleic acid comprising a sequence selected from the group consisting of SEQ ID NOS: 1-9,221, 15,366-15,392 and 15,516-15,527; the complementary sequence thereof; and a sequence at least about 80% identical thereto. The nucleic acid may be from 5-250 nucleotides in length. The nucleic acid may comprise a modified base.

Further provided is a probe comprising the nucleic acid. The probe may comprise at least 8-22 contiguous nucleotides complementary to SEQ ID NOS: 1-9,221, 15,366-15,392 and 15,516-15,527, or a variant thereof. The probe may also comprise at least 8-22 contiguous nucleotides complementary to a host microRNA differentially expressed in viral infection, or a variant thereof.

Also provided is a composition comprising the nucleic acid.

Further provided is a biochip comprising the nucleic acid.
Also provided is a vector comprising the nucleic acid.
Further provided is a host cell comprising the nucleic acid.
Also provided is a pharmaceutical composition comprising the nucleic acid as an active ingredient, and a composition comprising the vector.

Further provided is a method of preventing or treating viral infection or a condition associated with a viral infection in a subject in need thereof. The method may comprise administering to the subject an effective amount of a composition comprising a nucleic acid sequence selected from the group consisting of SEQ ID NOS: 1-9,221, 15,366-15,392 and 15,516-15,527; a complementary sequence thereof; and a sequence at least about 80% identical thereto. The viral infection may be caused by a virus selected from the group consisting of: HSV1, HSV2, RSV, EBV, Influenza A, HCV, HPV, HIV, HBV and Vaccinia virus. The condition associated with the viral infection may be selected from the group consisting of: Burkitt's lymphoma, nasopharingal carcinoma, ovarian carcinoma, cervical cancer, hepatitis, mononucleosis, genital herpes, encephalitis, influenza and bronchiolitis.

Also provided is a method for reducing the amount of virus replication in a target cell, where the target cell may be present in vitro or in vivo.

Further provided is the use of a nucleic acid comprising a nucleic acid sequence selected from the group consisting of SEQ ID NOS: 1-9,221, 15,366-15,392 and 15,516-15,527; a complementary sequence thereof; and a sequence at least about 80% identical thereto for the manufacture of a medicament for the treatment or prevention of viral infection.

Also provided is a method for modulating a nucleic acid. The method may comprise modulating a first nucleic acid comprising the nucleotide sequence selected from the group consisting of (a) any one of SEQ ID NOS: 9,222-15,365 and 15,393-15,515, (b) a complementary sequence of (a), and (c) sequence at least about 80% identical to (a) or (b).

The method may further comprise introducing a second nucleic acid to the first nucleic acid wherein the second nucleic acid is selected from the group consisting of (a) SEQ ID NOS: 1-9,221, 15,366-15,392, 15,516-15,527, and (b) sequence at least about 80% identical to (a), wherein the second nucleic acid modulates expression of the first nucleic acid. The first nucleic acid may be a miRNA target gene. The second nucleic acid may be a miRNA or siRNA.

Further provided is a method of inhibiting expression of a target gene in a cell. A nucleic acid may be introduced into the cell in an amount sufficient to inhibit expression of the target gene. The target gene may comprise a binding site substantially identical to SEQ ID NOS: 9,222-15,365 and 15,393-15,515, or a variant thereof. The nucleic acid may comprise a portion of SEQ ID NOS: 1-9,221, 15,366-15,392 and 15,516-15,527 or a variant thereof. Expression of a target gene may be inhibited in vitro or in vivo.

Also provided is a method of detecting viral infection of a cell comprising determining the expression level of a nucleic acid sequence selected from the group consisting of SEQ ID NOS: 1-9,221, 15,366-15,392 and 15,516-15,527; a complementary sequence thereto or a sequence at least about 80% identical thereto. The method of detecting viral infection may comprise a microRNA array, RT-PCR, or Northern blot analysis.

Further provided is a kit comprising the nucleic acid.

Also provided is a method of reducing the amount of virus replication in a target cell, which may comprise introducing an effective amount of a composition into a target cell infected with a virus. The composition may comprise a nucleic acid sequence selected from the group consisting of SEQ ID NOS: 1-9,221, 15,366-15,392 and 15,516-15,527; a complementary sequence thereof; and a sequence at least about 80% identical thereto. The target cell may be in vitro or in vivo. A subject may comprise said target cell. The virus may be HSV1, HSV2, RSV, EBV, Influenza A, HCV, HPV, HIV, HBV, or Vaccinia virus. The method may be used to treat a viral mediated disease condition in a subject in need thereof. The disease condition may be Burkitt's lymphoma, nasopharingal carcinoma, ovarian carcinoma, cervical cancer, hepatitis, mononucleosis, influenza, genital herpes, encephalitis, or bronchiolitis.

BRIEF DESCRIPTION OF THE SEQUENCE LISTING AND TABLES

Incorporated herein by reference are the sequence listing, which is a .txt file named, "Sequence Listing" (2,759 kb, created May 27, 2009); and the tables, which are .txt files named "Table 1" (283 kb), "Table 2" (36 kb),"Table 3" (217 kb),"Table 4" (1 kb),"Table 5" (9 kb),"Table 6" (190 kb),and "Table 7" (2 kb), all of which were created Nov. 29, 2006.

DETAILED DESCRIPTION

Figure 1:
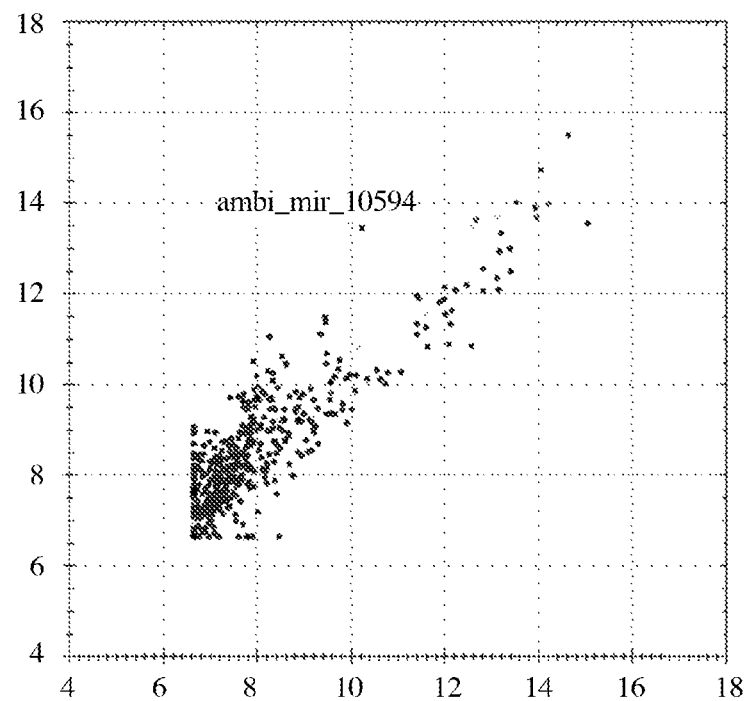
FIG. 1 shows microRNA expression profiling of respiratory syncytial virus (RSV) infected HEp2 cells as compared to uninfected control cells using miRdicator™ microRNA array. The expressed host microRNA AMB-10594 (SEQ ID NO: 15,374) is indicated.

During viral infection, viruses express specific miRNAs and alter host miRNA expression. Provided herein are compositions and methods to prevent or treat viral infection. Identification of specific miRNA signatures and the targets of these miRNAs induced by viruses may be used to identify cellular and viral genes required for viral infection.

The inventors have made the surprising discovery that the expression levels of several viral microRNAs (SEQ ID NOS: 15,375-15,387) and host microRNAs (SEQ ID NOS: 15,366-15,374) were altered following viral infection. Furthermore, different viruses produce distinct microRNAs expression patterns in various viral infected cells.

Specific viral and host miRNA nucleic acids may be used as novel therapeutics in the treatment of viral infections. The nucleic acids also be used in diagnostics for clinical and research settings including detection of latent infections. The disclosed viral and host miRNAs may be used to discover new cellular and viral drugs and drug targets.

Described herein is the expression of viral and host encoded microRNAs in viral infections by HSV1, HSV2, RSV, EBV, Influenza A, HCV, HPV and Vaccinia viruses.

Provided herein are nucleotide sequences of viral, and human miRNAs, precursors thereto, targets thereof and related sequences. Such nucleic acids may be used for diagnostic purposes, therapeutic purposes, and also for modifying target gene expression.

1. Definitions

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise. It must further be noted that the terms "and" and "or" may encompass both conjunctive and disjunctive meaning unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

"Animal" as used herein may mean fish, amphibians, reptiles, birds, and mammals, such as mice, rats, rabbits, goats, cats, dogs, cows, apes and humans.

"Attached" or "immobilized" as used herein to refer to a probe and a solid support may mean that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin Immobilization may also involve a combination of covalent and non-covalent interactions.

"Biological sample" as used herein may mean a sample of biological tissue or fluid that comprises nucleic acids. Such samples include, but are not limited to, tissue isolated from animals. Biological samples may also include sections of tissues such as biopsy and autopsy samples, frozen sections taken for histological purposes, blood, plasma, serum, sputum, stool, tears, mucus, urine, effusions, amniotic fluid, ascitic fluid, hair, and skin. Biological samples also include explants and primary and/or transformed cell cultures derived from patient tissues. A biological sample may be provided by removing a sample of cells from an animal, but can also be accomplished by using previously isolated cells (e.g., isolated by another person, at another time, and/or for another purpose), or by performing the methods described herein in vivo. Archival tissues, such as those having treatment or outcome history, may also be used.

"Complement" or "complementary" as used herein may mean Watson-Crick (e.g., A-T/U and C-G) or Hoogsteen base pairing between nucleotides or nucleotide analogs of nucleic acid molecules. A complement may be identical in length to a nucleic acid disclosed herein.

"Differential expression" may mean qualitative or quantitative differences in the temporal and/or cellular gene expression patterns within and among cells and tissue. Thus, a differentially expressed gene can qualitatively have its expression altered, including an activation or inactivation, in, e.g., normal versus disease tissue. Genes may be turned on or turned off in a particular state, relative to another state thus permitting comparison of two or more states. A qualitatively regulated gene will exhibit an expression pattern within a state or cell type that may be detectable by standard techniques. Some genes will be expressed in one state or cell type, but not in both. Alternatively, the difference in expression may be quantitative, e.g., in that expression is modulated, up-regulated, resulting in an increased amount of transcript, or down-regulated, resulting in a decreased amount of transcript. The degree to which expression differs need only be large enough to quantify via standard characterization techniques such as expression arrays, quantitative reverse transcriptase PCR, northern analysis, and RNase protection.

"Expression profile" as used herein may mean a genomic expression profile, e.g., an expression profile of microRNAs. Profiles may be generated by any convenient means for determining a level of a nucleic acid sequence e.g. quantitative hybridization of microRNA, labeled microRNA, amplified microRNA, cRNA, etc., quantitative PCR, ELISA for quantitation, and the like, and allow the analysis of differential gene expression between two samples. A subject or patient tumor sample, e.g., cells or collections thereof, e.g., tissues, is assayed. Samples are collected by any convenient method, as known in the art. Nucleic acid sequences of interest are nucleic acid sequences that are found to be predictive, including the nucleic acid sequences provided above, where the expression profile may include expression data for 5, 10, 20, 25, 50, 100 or more of, including all of the listed nucleic acid sequences. The term "expression profile" may also mean measuring the abundance of the nucleic acid sequences in the measured samples.

"Gene" used herein may be a genomic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA and antisense RNA. A gene may also be an miRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

"Host cell" used herein may mean a naturally occurring cell or a transformed cell that may contain a vector and may support the replication of the vector. Host cells may be cultured cells, explants, cells in vivo, and the like. Host cells may be prokaryotic cells such as E. coli, or eukaryotic cells such as yeast, insect, amphibian, or mammalian cells, such as CHO, HeLa.

"Identical" or "identity" used herein in the context of two or more nucleic acids or polypeptide sequences, may mean that the sequences have a specified percentage of residues that are the same over a specified region. The percentage may be calculated by comparing optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces staggered ends and the specified region of comparison includes only a single sequence, the residues of single sequence are included in the denominator but not the numerator of the calculation. When comparing DNA and RNA, thymine (T) and uracil (U) are considered equivalent. Identity may be performed manually or by using computer sequence algorithm such as BLAST or BLAST 2.0.

"Inhibit" as used herein may mean prevent, suppress, repress, reduce or eliminate.

"Label" as used herein may mean a composition detectable by spectroscopic, photochemical, biochemical, immunochemical, chemical, or other physical means. For example, useful labels include $P^{32}$, fluorescent dyes, electron-dense reagents, enzymes (e.g., as commonly used in an ELISA), biotin, digoxigenin, or haptens and other entities which can be made detectable. A label may be incorporated into nucleic acids and proteins at any position.

"Nucleic acid", "oligonucleotide" or "polynucleotide" used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to the target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. The nucleic acid may comprise a 2'-ribose replacement such as a 2'-O-methyl and 2'-fluoro group, as described in U.S. Pat. No. 7,138,517, the contents of which are incorporated herein by reference. Modified nucleotides also include nucleotides conjugated with cholesterol through a hydroxyprolinol linkage as described in Krutzfeldt et al., Nature 438:685-689 (2005), Soutschek et al., Nature 432:173-178 (2004), and U.S. Patent Publication No. 20050107325, which are incorporated herein by reference. Modified nucleotides and nucleic acids may also include locked nucleic acids (LNA), as described in U.S. Patent No. 20020115080, which is incorporated herein by reference. Additional modified nucleotides and nucleic acids are described in U.S. Patent Publication No. 20050182005, which is incorporated herein by reference. Modifications of the ribose-phosphate backbone may be done for a variety of reasons, e.g., to increase the stability and half-life of such molecules in physiological environments or as probes on a biochip. Mixtures of naturally occurring nucleic acids and analogs may be made; alternatively, mixtures of different nucleic acid analogs, and mixtures of naturally occurring nucleic acids and analogs may be made.

"Operably linked" used herein may mean that expression of a gene is under the control of a promoter with which it is spatially connected. A promoter may be positioned 5' (upstream) or 3' (downstream) of a gene under its control. The distance between the promoter and the gene may be approximately the same as the distance between that promoter and the gene it controls in the gene from which the promoter is derived. As is known in the art, variation in this distance may be accommodated without loss of promoter function.

"Probe" as used herein may mean an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches that will interfere with hybridization between the target sequence and a single stranded nucleic acid described herein. However, if the number of mismatches is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

"Promoter" as used herein may mean a synthetic or naturally-derived molecule which is capable of conferring, activating or enhancing expression of a nucleic acid in a cell. A promoter may comprise one or more specific regulatory elements to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Reducing the amount of virus replication" used herein may mean that the level or quantity of the target viral genome in the target cell is reduced by at least about 2-fold to 100-fold or more, as compared to a control, i.e., an identical target cell not treated according to the subject methods.

"Selectable marker" used herein may mean any gene which confers a phenotype on a cell in which it is expressed to facilitate the identification and/or selection of cells which are transfected or transformed with a genetic construct. Representative examples of selectable markers include the ampicillin-resistance gene ($Amp^r$), tetracycline-resistance gene ($Tc^r$), bacterial kanamycin-resistance gene ($Kan^r$), zeocin resistance gene, the AURI-C gene which confers resistance to the antibiotic aureobasidin A, phosphinothricin-resistance gene, neomycin phosphotransferase gene (nptII), hygromycin-resistance gene, beta-glucuronidase (GUS) gene, chloramphenicol acetyltransferase (CAT) gene, green fluorescent protein-encoding gene and luciferase gene.

"Stringent hybridization conditions" used herein may mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Generally, stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Substantially complementary" used herein may mean that a first sequence is at least 60%-99% identical to the complement of a second sequence over a region of 8-50 or more nucleotides, or that the two sequences hybridize under stringent hybridization conditions.

"Substantially identical" used herein may mean that a first and second sequence are at least 60%-99% identical over a region of 8-50 or more nucleotides or amino acids, or with respect to nucleic acids, if the first sequence is substantially complementary to the complement of the second sequence.

"Subject" used herein may mean a mammal, such as a human.

"Target" as used herein may mean a polynucleotide that may be bound by one or more probes under stringent hybridization conditions.

"Terminator" used herein may mean a sequence at the end of a transcriptional unit which signals termination of transcription. A terminator may be a 3'-non-translated DNA sequence containing a polyadenylation signal, which may facilitate the addition of polyadenylate sequences to the 3'-end of a primary transcript. A terminator may be derived from sources including viral, bacterial, fungal, plants, insects, and animals. Representative examples of terminators include the SV40 polyadenylation signal, HSV TK polyadenylation signal, CYC1 terminator, ADH terminator, SPA terminator, nopaline synthase (NOS) gene terminator of *Agrobacterium tumefaciens*, the terminator of the Cauliflower mosaic virus (CaMV) 35S gene, the zein gene terminator from *Zea mays*, the Rubisco small subunit gene (SSU) gene terminator sequences, subclover stunt virus (SCSV) gene sequence terminators, rho-independent *E. coli* terminators, and the lacZ alpha terminator.

"Treat" or "treating" used herein when referring to protection of an animal from a condition may mean preventing, suppressing, repressing, or eliminating the condition. Preventing the condition involves administering a composition described herein to an animal prior to onset of the condition. Suppressing the condition involves administering the composition to an animal after induction of the condition but before its clinical appearance. Repressing the condition involves administering the composition to an animal after clinical appearance of the condition such that the condition is reduced or prevented from worsening. Elimination of the condition involves administering the composition to an animal after clinical appearance of the condition such that the animal no longer suffers from the condition.

"Therapeutically effective amount" used herein or "therapeutically efficient" as to a drug dosage may refer to dosage that provides the specific pharmacological response for which the drug is administered in a significant number of subjects in need of such treatment. The "therapeutically effective amount" may vary according, for example, the physical condition of the patient, the age of the patient and the severity of the disease.

"Unit dosage form," used herein may refer to a physically discrete unit suitable as a unitary dosage for a human or animal subject. Each unit may contain a predetermined quantity of a composition described herein, calculated in an amount sufficient to produce a desired effect in association with a pharmaceutically acceptable diluent, carrier or vehicle. The specifications for a unit dosage form may depend on the particular composition employed and the effect to be achieved, and the pharmacodynamics associated with the composition in the host.

"Variant" used herein to refer to a nucleic acid may mean (i) a portion of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Vector" used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector that integrates into a host genome.

"Wild type" used herein to refer to a sequence may mean a coding, non-coding or interface sequence that may be an allelic form of a sequence that performs the natural or normal function for that sequence. Wild type sequences may include multiple allelic forms of a cognate sequence, for example, multiple alleles of a wild type sequence may encode silent or conservative changes to the protein sequence that a coding sequence encodes.

2. MicroRNA

While not being bound by theory, a gene coding for a miRNA may be transcribed leading to production of an miRNA precursor known as the pri-miRNA. The pri-miRNA may be part of a polycistronic RNA comprising multiple pri-miRNAs. The pri-miRNA may form a hairpin with a stem and loop. The stem may comprise mismatched bases.

The hairpin structure of the pri-miRNA may be recognized by Drosha, which is an RNase III endonuclease. Drosha may recognize terminal loops in the pri-miRNA and cleave approximately two helical turns into the stem to produce a 30 200 nt precursor known as the pre-miRNA. Drosha may cleave the pri-miRNA with a staggered cut typical of RNase III endonucleases yielding a pre-miRNA stem loop with a 5' phosphate and ~2 nucleotide 3' overhang. Approximately one helical turn of the stem (~10 nucleotides) extending beyond the Drosha cleavage site may be essential for efficient processing. The pre-miRNA may then be actively transported from the nucleus to the cytoplasm by Ran-GTP and the export receptor Ex-portin-5.

The pre-miRNA may be recognized by Dicer, which is also an RNase III endonuclease. Dicer may recognize the double-stranded stem of the pre-miRNA. Dicer may also recognize the 5' phosphate and 3' overhang at the base of the stem loop. Dicer may cleave off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. MiRNA* sequences may be found in libraries of cloned miRNAs but typically at lower frequency than the miRNAs.

Although initially present as a double-stranded species with miRNA*, the miRNA may eventually become incorporated as a single-stranded RNA into a ribonucleoprotein complex known as the RNA-induced silencing complex (RISC). Various proteins can form the RISC, which can lead to variability in the specificity for miRNA/miRNA* duplexes, the binding site of the target gene, the activity of the miRNA (repress or activate), and which strand of the miRNA/miRNA* duplex is loaded in to the RISC.

When the miRNA strand of the miRNA:miRNA* duplex is loaded into the RISC, the miRNA* may be removed and degraded. The strand of the miRNA:miRNA* duplex that is loaded into the RISC may be the strand whose 5' end is less tightly paired. In cases where both ends of the miRNA:miRNA* have roughly equivalent 5' pairing, both miRNA and miRNA* may have gene silencing activity.

The RISC may identify target nucleic acids based on high levels of complementarity between the miRNA and the mRNA, especially by nucleotides 2-8 of the miRNA. Only one case has been reported in animals where the interaction between the miRNA and its target was along the entire length of the miRNA. This was shown for mir-196 and Hox B8 and it was further shown that mir-196 mediates the cleavage of the Hox B8 mRNA (Yekta et al 2004, Science 304-594). Otherwise, such interactions are known only in plants (Bartel & Bartel 2003, Plant Physiol 132-709).

A number of studies have looked at the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 GenesDev 2004-504). However, other parts of the microRNA may also participate in mRNA binding. Moreover, sufficient base pairing at the 3' end can compensate for insufficient pairing at the 5' end (Brennecke et al, 2005 PLoS 3-e85). Computation studies, analyzing miRNA binding on whole genomes have suggested a specific role for bases 2-7 at the 5' end of the miRNA in target binding but the role of the first nucleotide, found usually to be "A" was also recognized (Lewis et at 2005 Cell 120-15). Similarly, nucleotides 1-7 or 2-8 were used to identify and validate targets by Krek et al (2005, Nat Genet 37-495).

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

MiRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut may be between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and the binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

3. Nucleic Acid

A nucleic acid is provided herein. The nucleic acid may comprise the sequence of any one of SEQ ID NOS: 1-15,527 or a variant thereof. The variant may be a complement of the referenced nucleotide sequence. The variant may also be a nucleotide sequence that is substantially identical to the referenced nucleotide sequence or the complement thereof. The variant may also be a nucleotide sequence which hybridizes under stringent conditions to the referenced nucleotide sequence, complements thereof, or nucleotide sequences substantially identical thereto. The nucleic acid may have a length of at least 10-250 nucleotides. The nucleic acid may comprise a modified base. The nucleic acid may be synthesized or expressed in a cell (in vitro or in vivo) using a synthetic gene described herein. The nucleic acid may be synthesized as a single strand molecule and hybridized to a substantially complementary nucleic acid to form a duplex.

LENGTHY TABLES

The patent contains a lengthy table section. A copy of the table is available in electronic form from the USPTO web site (http://seqdata.uspto.gov/?pageRequest=docDetail&DocID=US08481506B2). An electronic copy of the table will also be available from the USPTO upon request and payment of the fee set forth in 37 CFR 1.19(b)(3).

a. Nucleic acid complex

The nucleic acid may further comprise one or more of the following: a peptide, a protein, a RNA-DNA hybrid, an antibody, an antibody fragment, a Fab fragment, and an aptamer.

b. Pri-miRNA

The nucleic acid may comprise a sequence of a pri-miRNA or a variant thereof. The pri-miRNA sequence may comprise from 45-30,000, 50-25,000, 100-20,000, 1,000-1,500 or 80-100 nucleotides. The sequence of the pri-miRNA may comprise a pre-miRNA, miRNA and miRNA*, as set forth herein, and variants thereof. The sequence of the pri-miRNA may comprise the sequence of any one of SEQ ID NOS: 1-15,527 or a variant thereof.

The pri-miRNA may form a hairpin structure. The hairpin may comprise first and second nucleic acid sequence that are substantially complementary. The first and second nucleic acid sequence may be from 37-50 nucleotides. The first and second nucleic acid sequence may be separated by a third sequence of from 8-12 nucleotides. The hairpin structure may have a free energy less than −25 Kcal/mole as calculated by the Vienna algorithm with default parameters, as described in Hofacker et al., Monatshefte f. Chemie 125: 167-188 (1994), the contents of which are incorporated herein. The hairpin may comprise a terminal loop of 4-20, 8-12 or 10 nucleotides. The pri-miRNA may comprise at least 19% adenosine nucleotides, at least 16% cytosine nucleotides, at least 23% thymine nucleotides and at least 19% guanine nucleotides.

c. Pre-miRNA

The nucleic acid may also comprise a sequence of a pre-miRNA or a variant thereof. The pre-miRNA sequence may comprise from 45-200, 60-80 or 60-70 nucleotides. The sequence of the pre-miRNA may comprise a miRNA and a miRNA* as set forth herein. The sequence of the pre-miRNA may also be that of a pri-miRNA excluding from 0-160 nucleotides from the 5' and 3' ends of the pri-miRNA. The sequence of the pre-miRNA may comprise the sequence of any one of SEQ ID NOS: 1-15,527 or a variant thereof.

d. MiRNA

The nucleic acid may also comprise a sequence of a miRNA (including miRNA*) or a variant thereof. The miRNA sequence may comprise from 13-33, 18-24 or 21-23 nucleotides. The miRNA may also comprise a total of at least 5-40 nucleotides. The sequence of the miRNA may be the first 13-33 nucleotides of the pre-miRNA. The sequence of the miRNA may also be the last 13-33 nucleotides of the pre-miRNA. The sequence of the miRNA may be differentially expressed during a viral infection, and may comprise the sequence of any one of SEQ ID NOS: 1-9,221, 15,366-15,392, 15,516-15,527, or a variant thereof as indicated in Table 1 and Table 8.

TABLE 8

The host and viral microRNAs which were differentially expressed upon viral infection

| MID | HIDs | microRNA name | Organism |
|---|---|---|---|
| 15,366 | 15,379 | hsa-miR-181a | *Homo sapiens* |
| 15,367 | 15,380 | hsa-miR-193a | *Homo sapiens* |
| 15,368 | 15,381 | hsa-miR-107 | *Homo sapiens* |
| 15,369 | 15,382 | hsa-miR-103 | *Homo sapiens* |
| 15,370 | 15,383 | hsa-miR-296 | *Homo sapiens* |
| 15,371 | 15,384 | hsa-miR-574 | *Homo sapiens* |
| 15,372 | 15,385 | hsa-miR-210 | *Homo sapiens* |
| 15,373 | 15,386 | hsa-miR-21 | *Homo sapiens* |
| 15,374 | 15,387 | RG__AMB_10594 | *Homo sapiens* |
| 15,375 | 15,388 | hsv1-miR-H1 | Human herpesvirus 1 |
| 15,376 | 15,389 15,392 | RG__HSV2__Pred13 | Human herpesvirus 2 |
| 15,377 | 15,389 15,392 | RG__HSV2__8 | Human herpesvirus 2 |
| 15,378 | 15,390 15,391 | RG__fluA12 | Influenza A virus |

MID: SEQ ID NO of the mature microRNA sequence
HIDs: SEQ ID NO(S) of the hairpin microRNA precursor
microRNA name: The miRBase registry Sanger 9.2 microRNA name, excluding cases in which the names begins with "RG". In these cases the names are internal miRNA names of Rosetta Genomics.
Organism: The microRNA organism.

e. Anti-miRNA

The nucleic acid may also comprise a sequence of an anti-miRNA that is capable of blocking the activity of a miRNA or miRNA*, such as by binding to the pri-miRNA, pre-miRNA, miRNA or miRNA* (e.g. antisense or RNA silencing), or by binding to the target binding site. The anti-miRNA may comprise a total of 5-100 or 10-60 nucleotides. The anti-miRNA may also comprise a total of at least 5-40 nucleotides. The sequence of the anti-miRNA may comprise (a) at least 5 nucleotides that are substantially identical or complementary to the 5' of a miRNA and at least 5-12 nucleotides that are substantially complementary to the flanking regions of the target site from the 5' end of the miRNA, or (b) at least 5-12 nucleotides that are substantially identical or complementary to the 3' of a miRNA and at least 5 nucleotide that are substantially complementary to the flanking region of the target site from the 3' end of the miRNA. The sequence of the anti-miRNA may comprise the complement of any one of SEQ ID NOS: 1-15,527 or a variant thereof.

f. Binding Site of Target

The nucleic acid may also comprise a sequence of a target microRNA binding site, or a variant thereof. The target site sequence may comprise a total of 5-100 or 10-60 nucleotides. The target site sequence may also comprise a total of at least 5-63 nucleotides. The target site sequence may comprise at least 5 nucleotides of the sequence of any one of SEQ ID NOS: 9,222-15,365 and 15,393-15,515 as indicated in Tables 3 and 9.

TABLE 9

The miRNAs and their predicted binding sites

| microRNA name | MID | Organism | Target gene name | BS SEQ ID NO | Gene Ontology ID |
|---|---|---|---|---|---|
| hsa-miR-181a | 15,366 | *Homo sapiens* | BCL2 | 15,436 | GO:0006959 |
| hsa-miR-181a | 15,366 | *Homo sapiens* | BCL2 | 15,436 | GO:0051607 |
| hsa-miR-181a | 15,366 | *Homo sapiens* | CARD11 | 15,416 | GO:0050776 |
| hsa-miR-181a | 15,366 | *Homo sapiens* | CBLB | 15,506 | GO:0006955 |
| hsa-miR-181a | 15,366 | *Homo sapiens* | CCL8 | 15,477 | GO:0006955 |
| hsa-miR-181a | 15,366 | *Homo sapiens* | CCL8 | 15,477 | GO:0009615 |
| hsa-miR-181a | 15,366 | *Homo sapiens* | CD4 | 15,471 | GO:0006955 |
| hsa-miR-181a | 15,366 | *Homo sapiens* | CD59 | 15,450 | GO:0006955 |
| hsa-miR-181a | 15,366 | *Homo sapiens* | CXCL5 | 15,419 | GO:0006955 |
| hsa-miR-181a | 15,366 | *Homo sapiens* | ETS1 | 15,499 | GO:0006955 |
| hsa-miR-181a | 15,366 | *Homo sapiens* | FAS | 15,502 | GO:0006955 |
| hsa-miR-181a | 15,366 | *Homo sapiens* | GBP6 | 15,489 | GO:0006955 |
| hsa-miR-181a | 15,366 | *Homo sapiens* | IFNA17 | 15,511 | GO:0009615 |
| hsa-miR-181a | 15,366 | *Homo sapiens* | IL2 | 15,483 | GO:0006955 |
| hsa-miR-181a | 15,366 | *Homo sapiens* | LIF | 15,400 | GO:0006955 |
| hsa-miR-181a | 15,366 | *Homo sapiens* | MS4A1 | 15,494 | GO:0006955 |
| hsa-miR-181a | 15,366 | *Homo sapiens* | MS4A1 | 15,497 | GO:0006955 |
| hsa-miR-181a | 15,366 | *Homo sapiens* | OPRK1 | 15,425 | GO:0006955 |
| hsa-miR-181a | 15,366 | *Homo sapiens* | POLA | 15,453 | GO:0009615 |
| hsa-miR-181a | 15,366 | *Homo sapiens* | SAMHD1 | 15,399 | GO:0006955 |
| hsa-miR-181a | 15,366 | *Homo sapiens* | SEMA3C | 15,393 | GO:0006955 |
| hsa-miR-181a | 15,366 | *Homo sapiens* | TNF | 15,428 | GO:0006959 |
| hsa-miR-181a | 15,366 | *Homo sapiens* | TNF | 15,428 | GO:0009615 |
| hsa-miR-181a | 15,366 | *Homo sapiens* | TNFAIP1 | 15,455 | GO:0006955 |
| hsa-miR-181a | 15,366 | *Homo sapiens* | TNFSF4 | 15,496 | GO:0006955 |
| hsa-miR-193a | 15,367 | *Homo sapiens* | CD97 | 15,468 | GO:0006955 |
| hsa-miR-193a | 15,367 | *Homo sapiens* | TNFAIP1 | 15,495 | GO:0006955 |
| hsa-miR-107 | 15,368 | *Homo sapiens* | ARL6IP2 | 15,446 | GO:0006955 |
| hsa-miR-107 | 15,368 | *Homo sapiens* | BST1 | 15,395 | GO:0006959 |
| hsa-miR-107 | 15,368 | *Homo sapiens* | CCL13 | 15,460 | GO:0006955 |
| hsa-miR-107 | 15,368 | *Homo sapiens* | EBI2 | 15,456 | GO:0006955 |
| hsa-miR-107 | 15,368 | *Homo sapiens* | FCGR2A | 15,487 | GO:0006955 |
| hsa-miR-107 | 15,368 | *Homo sapiens* | FCGR2B | 15,488 | GO:0006955 |
| hsa-miR-107 | 15,368 | *Homo sapiens* | IFIT1L | 15,426 | GO:0006955 |
| hsa-miR-107 | 15,368 | *Homo sapiens* | IFNAR1 | 15,516 | GO:0009615 |
| hsa-miR-107 | 15,368 | *Homo sapiens* | IL15 | 15,421 | GO:0006955 |
| hsa-miR-107 | 15,368 | *Homo sapiens* | IL16 | 15,447 | GO:0006955 |
| hsa-miR-107 | 15,368 | *Homo sapiens* | IL1RAP | 15,402 | GO:0006955 |
| hsa-miR-107 | 15,368 | *Homo sapiens* | MICB | 15,433 | GO:0006955 |
| hsa-miR-107 | 15,368 | *Homo sapiens* | OAS3 | 15,444 | GO:0006955 |
| hsa-miR-107 | 15,368 | *Homo sapiens* | SPON2 | 15,462 | GO:0006955 |
| hsa-miR-107 | 15,368 | *Homo sapiens* | TNF | 15,424 | GO:0006959 |
| hsa-miR-107 | 15,368 | *Homo sapiens* | TNF | 15,424 | GO:0009615 |
| hsa-miR-103 | 15,369 | *Homo sapiens* | ARL6IP2 | 15,446 | GO:0006955 |
| hsa-miR-103 | 15,369 | *Homo sapiens* | BST1 | 15,395 | GO:0006959 |
| hsa-miR-103 | 15,369 | *Homo sapiens* | CCL13 | 15,460 | GO:0006955 |
| hsa-miR-103 | 15,369 | *Homo sapiens* | EBI2 | 15,456 | GO:0006955 |
| hsa-miR-103 | 15,369 | *Homo sapiens* | FCGR2A | 15,487 | GO:0006955 |
| hsa-miR-103 | 15,369 | *Homo sapiens* | FCGR2B | 15,488 | GO:0006955 |
| hsa-miR-103 | 15,369 | *Homo sapiens* | IFIT1L | 15,426 | GO:0006955 |
| hsa-miR-103 | 15,369 | *Homo sapiens* | IFNAR1 | 15,516 | GO:0009615 |
| hsa-miR-103 | 15,369 | *Homo sapiens* | IL15 | 15,421 | GO:0006955 |
| hsa-miR-103 | 15,369 | *Homo sapiens* | IL16 | 15,447 | GO:0006955 |
| hsa-miR-103 | 15,369 | *Homo sapiens* | IL1RAP | 15,402 | GO:0006955 |
| hsa-miR-103 | 15,369 | *Homo sapiens* | MICB | 15,433 | GO:0006955 |
| hsa-miR-103 | 15,369 | *Homo sapiens* | OAS3 | 15,444 | GO:0006955 |
| hsa-miR-103 | 15,369 | *Homo sapiens* | SPON2 | 15,462 | GO:0006955 |
| hsa-miR-103 | 15,369 | *Homo sapiens* | TNF | 15,424 | GO:0006959 |
| hsa-miR-103 | 15,369 | *Homo sapiens* | TNF | 15,424 | GO:0009615 |
| hsa-miR-296 | 15,370 | *Homo sapiens* | CD22 | 15,397 | GO:0006955 |
| hsa-miR-296 | 15,370 | *Homo sapiens* | CD6 | 15,405 | GO:0006955 |
| hsa-miR-296 | 15,370 | *Homo sapiens* | CD6 | 15,440 | GO:0006955 |
| hsa-miR-296 | 15,370 | *Homo sapiens* | CD8A | 15,466 | GO:0006955 |
| hsa-miR-296 | 15,370 | *Homo sapiens* | CXCL10 | 15,501 | GO:0006955 |
| hsa-miR-296 | 15,370 | *Homo sapiens* | GBP4 | 15,490 | GO:0006955 |
| hsa-miR-296 | 15,370 | *Homo sapiens* | GCK | 15,464 | GO:0006955 |
| hsa-miR-296 | 15,370 | *Homo sapiens* | HLA-DOA | 15,415 | GO:0006955 |
| hsa-miR-296 | 15,370 | *Homo sapiens* | LAT2 | 15,396 | GO:0006955 |
| hsa-miR-296 | 15,370 | *Homo sapiens* | LIF | 15,470 | GO:0006955 |
| hsa-miR-296 | 15,370 | *Homo sapiens* | MAP4K2 | 15,439 | GO:0006955 |
| hsa-miR-296 | 15,370 | *Homo sapiens* | PVRL1 | 15,465 | GO:0006955 |
| hsa-miR-296 | 15,370 | *Homo sapiens* | SQSTM1 | 15,475 | GO:0006955 |
| hsa-miR-296 | 15,370 | *Homo sapiens* | TNFSF15 | 15,504 | GO:0006955 |
| hsa-miR-296 | 15,370 | *Homo sapiens* | VIPR1 | 15,458 | GO:0006955 |
| hsa-miR-574 | 15,371 | *Homo sapiens* | IL28RA | 15,486 | GO:0050691 |

TABLE 9-continued

The miRNAs and their predicted binding sites

| microRNA name | MID | Organism | Target gene name | BS SEQ ID NO | Gene Ontology ID |
|---|---|---|---|---|---|
| hsa-miR-210 | 15,372 | *Homo sapiens* | CD59 | 15,406 | GO:0006955 |
| hsa-miR-21 | 15,373 | *Homo sapiens* | CCL1 | 15,513 | GO:0006955 |
| hsa-miR-21 | 15,373 | *Homo sapiens* | CCL20 | 15,512 | GO:0006955 |
| hsa-miR-21 | 15,373 | *Homo sapiens* | CTSC | 15,418 | GO:0006955 |
| hsa-miR-21 | 15,373 | *Homo sapiens* | FASLG | 15,401 | GO:0006955 |
| hsa-miR-21 | 15,373 | *Homo sapiens* | IL12A | 15,515 | GO:0006955 |
| hsa-miR-21 | 15,373 | *Homo sapiens* | LILRB4 | 15,430 | GO:0006955 |
| hsa-miR-21 | 15,373 | *Homo sapiens* | PAG1 | 15,482 | GO:0006955 |
| hsa-miR-21 | 15,373 | *Homo sapiens* | ST6GAL1 | 15,484 | GO:0006959 |
| AMB__10594 | 15,374 | *Homo sapiens* | C5AR1 | 15,445 | GO:0006955 |
| AMB__10594 | 15,374 | *Homo sapiens* | CD74 | 15,461 | GO:0006955 |
| AMB__10594 | 15,374 | *Homo sapiens* | CD79B | 15,437 | GO:0006955 |
| AMB__10594 | 15,374 | *Homo sapiens* | CX3CL1 | 15,413 | GO:0006955 |
| AMB__10594 | 15,374 | *Homo sapiens* | DBNL | 15,451 | GO:0006955 |
| AMB__10594 | 15,374 | *Homo sapiens* | HLA-DOA | 15,435 | GO:0006955 |
| AMB__10594 | 15,374 | *Homo sapiens* | IFITM1 | 15,442 | GO:0006955 |
| AMB__10594 | 15,374 | *Homo sapiens* | IL1R1 | 15,474 | GO:0006955 |
| AMB__10594 | 15,374 | *Homo sapiens* | IL6ST | 15,427 | GO:0006955 |
| AMB__10594 | 15,374 | *Homo sapiens* | MBP | 15,443 | GO:0006955 |
| AMB__10594 | 15,374 | *Homo sapiens* | MS4A2 | 15,478 | GO:0006959 |
| AMB__10594 | 15,374 | *Homo sapiens* | NCR3 | 15,459 | GO:0006955 |
| AMB__10594 | 15,374 | *Homo sapiens* | TNFSF8 | 15,414 | GO:0006955 |
| AMB__10594 | 15,374 | *Homo sapiens* | TOLLIP | 15,411 | GO:0006955 |
| hsv1-miR-H1 | 15,375 | Human herpesvirus 1 | ADA | 15,448 | GO:0006955 |
| hsv1-miR-H1 | 15,375 | Human herpesvirus 1 | ANXA11 | 15,409 | GO:0006955 |
| hsv1-miR-H1 | 15,375 | Human herpesvirus 1 | CXCL9 | 15,473 | GO:0006955 |
| hsv1-miR-H1 | 15,375 | Human herpesvirus 1 | HLA-DOB | 15,469 | GO:0006955 |
| hsv1-miR-H1 | 15,375 | Human herpesvirus 1 | IFIT5 | 15,423 | GO:0006955 |
| hsv1-miR-H1 | 15,375 | Human herpesvirus 1 | OASL | 15,412 | GO:0006955 |
| hsv1-miR-H1 | 15,375 | Human herpesvirus 1 | POU2AF1 | 15,441 | GO:0006959 |
| hsv1-miR-H1 | 15,375 | Human herpesvirus 1 | PTGER4 | 15,420 | GO:0006955 |
| hsv1-miR-H1 | 15,375 | Human herpesvirus 1 | SERPINB4 | 15,505 | GO:0006955 |
| hsv1-miR-H1 | 15,375 | Human herpesvirus 1 | SLA2 | 15,454 | GO:0050776 |
| hsv1-miR-H1 | 15,375 | Human herpesvirus 1 | ST6GAL1 | 15,422 | GO:0006959 |
| hsv1-miR-H1 | 15,375 | Human herpesvirus 1 | TCF1 | 15,498 | GO:0006955 |
| HSV2__Pred13 | 15,376 | Human herpesvirus 2 | CD24 | 15,480 | GO:0006959 |
| HSV2__Pred13 | 15,376 | Human herpesvirus 2 | IL16 | 15,493 | GO:0006955 |
| HSV2__Pred13 | 15,376 | Human herpesvirus 2 | IL1A | 15,431 | GO:0006955 |
| HSV2__Pred13 | 15,376 | Human herpesvirus 2 | IL1RL1 | 15,434 | GO:0006955 |
| HSV2__Pred13 | 15,376 | Human herpesvirus 2 | MBP | 15,507 | GO:0006955 |
| HSV2__Pred13 | 15,376 | Human herpesvirus 2 | OLR1 | 15,394 | GO:0006955 |
| HSV2__Pred13 | 15,376 | Human herpesvirus 2 | TNFAIP1 | 15,403 | GO:0006955 |
| HSV2__Pred13 | 15,376 | Human herpesvirus 2 | TRIM5 | 15,404 | GO:0009615 |
| HSV2__Pred13 | 15,376 | Human herpesvirus 2 | VIPR1 | 15,410 | GO:0006955 |
| HSV2__8 | 15,377 | Human herpesvirus 2 | ABCE1 | 15,472 | GO:0009615 |
| HSV2__8 | 15,377 | Human herpesvirus 2 | CAST | 15,514 | GO:0006955 |
| HSV2__8 | 15,377 | Human herpesvirus 2 | CCL20 | 15,429 | GO:0006955 |
| HSV2__8 | 15,377 | Human herpesvirus 2 | CCR2 | 15,476 | GO:0006955 |
| HSV2__8 | 15,377 | Human herpesvirus 2 | CXCL3 | 15,417 | GO:0006955 |
| HSV2__8 | 15,377 | Human herpesvirus 2 | DUOX2 | 15,408 | GO:0009615 |
| fluA12 | 15,378 | Influenza A virus | C19orf2 | 15,479 | GO:0009615 |
| fluA12 | 15,378 | Influenza A virus | CAST | 15,467 | GO:0006955 |
| fluA12 | 15,378 | Influenza A virus | CBLB | 15,509 | GO:0006955 |
| fluA12 | 15,378 | Influenza A virus | CCL8 | 15,438 | GO:0006955 |
| fluA12 | 15,378 | Influenza A virus | CCL8 | 15,438 | GO:0009615 |
| fluA12 | 15,378 | Influenza A virus | CCR9 | 15,432 | GO:0006955 |
| fluA12 | 15,378 | Influenza A virus | CLEC6A | 15,463 | GO:0006955 |
| fluA12 | 15,378 | Influenza A virus | CTSS | 15,481 | GO:0006955 |
| fluA12 | 15,378 | Influenza A virus | CXCL12 | 15,485 | GO:0006955 |
| fluA12 | 15,378 | Influenza A virus | CXCL12 | 15,485 | GO:0009615 |
| fluA12 | 15,378 | Influenza A virus | CXCL5 | 15,510 | GO:0006955 |
| fluA12 | 15,378 | Influenza A virus | CXCL6 | 15,500 | GO:0006955 |
| fluA12 | 15,378 | Influenza A virus | IFNGR2 | 15,451 | GO:0009615 |
| fluA12 | 15,378 | Influenza A virus | IL1RAP | 15,508 | GO:0006955 |
| fluA12 | 15,378 | Influenza A virus | MADCAM1 | 15,407 | GO:0006955 |
| fluA12 | 15,378 | Influenza A virus | MS4A1 | 15,492 | GO:0006955 |
| fluA12 | 15,378 | Influenza A virus | OAS3 | 15,457 | GO:0006955 |

TABLE 9-continued

The miRNAs and their predicted binding sites

| microRNA name | MID | Organism | Target gene name | BS SEQ ID NO | Gene Ontology ID |
|---|---|---|---|---|---|
| fluA12 | 15,378 | Influenza A virus | SMAD3 | 15,503 | GO:0050776 |
| fluA12 | 15,378 | Influenza A virus | TNFRSF11A | 15,491 | GO:0006955 |
| fluA12 | 15,378 | Influenza A virus | ZF | 15,398 | GO:0009615 | microRNA name: The miRBase registry (Release 9.2) microRNA name, excluding cases in which the names begins with "RG". In these cases the names are internal miRNA names of Rosetta Genomics.
MID: SEQ ID NO of the mature microRNA
Target gene name: Target gene name according to RefSeq database
BS SEQ ID NO: The SEQ ID NO of the binding site of the microRNA to the 3' UTR of the target gene.
Gene Ontology ID: Gene Ontology (GO) ID. All are related to viral infection and to the immune response, as described in Table 10.

TABLE 10

The description of Gene Ontology IDs

| GOid | Description |
|---|---|
| GO:0009615 | response to virus |
| GO:0051607 | defense response to virus |
| GO:0050691 | regulation of antiviral response by host |
| GO:0006959 | humoral immune response |
| GO:0006955 | immune response |
| GO:0050776 | regulation of immune response |

Description: The Gene Ontology description of GO ID

4. Synthetic Gene

A synthetic gene is also provided comprising a nucleic acid described herein operably linked to a transcriptional and/or translational regulatory sequence. The synthetic gene may be capable of modifying the expression of a target gene with a binding site for a nucleic acid described herein. Expression of the target gene may be modified in a cell, tissue or organ. The synthetic gene may be synthesized or derived from naturally-occurring genes by standard recombinant techniques. The synthetic gene may also comprise terminators at the 3'-end of the transcriptional unit of the synthetic gene sequence. The synthetic gene may also comprise a selectable marker.

5. Vector

A vector is also provided comprising a nucleic acid described herein, such as a pri-miRNA, pre-miRNA, miRNA, anti-miRNA, target gene binding site, or synthetic gene. The vector may be an expression vector. An expression vector may comprise additional elements. For example, the expression vector may have two replication systems allowing it to be maintained in two organisms, e.g., in one host cell for expression and in a second host cell (e.g., bacteria) for cloning and amplification. For integrating expression vectors, the expression vector may contain at least one sequence homologous to the host cell genome, and preferably two homologous sequences which flank the expression construct. The integrating vector may be directed to a specific locus in the host cell by selecting the appropriate homologous sequence for inclusion in the vector. The vector may also comprise a selectable marker gene to allow the selection of transformed host cells.

6. Host Cell

A host cell is also provided comprising a vector, synthetic gene or nucleic acid described herein. The cell may be a bacterial, fungal, plant, insect or animal cell. For example, the host cell line may be DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3.times.63-Ag3.653 (mouse myeloma), BFA-1c1BPT (bovine endothelial cells), RAJI (human lymphocyte) and 293 (human kidney). Host cell lines may be available from commercial services, the American Tissue Culture Collection or from published literature.

7. Probes

A probe is also provided comprising a nucleic acid described herein. Probes may be used for screening and diagnostic methods, as outlined herein. The probe may be attached or immobilized to a solid substrate, such as a biochip.

The probe may have a length of from 8 to 500, 10 to 100 or 20 to 60 nucleotides. The probe may also have a length of at least 8-300 nucleotides. The probe may further comprise a linker sequence of from 10-60 nucleotides.

8. Biochip

A biochip is also provided. The biochip may comprise a solid substrate comprising an attached probe or plurality of probes described herein. The probes may be capable of hybridizing to a target sequence under stringent hybridization conditions. The probes may be attached at spatially defined addresses on the substrate. More than one probe per target sequence may be used, with either overlapping probes or probes to different sections of a particular target sequence. The probes may be capable of hybridizing to target sequences associated with a single disorder. The probes may either be synthesized first, with subsequent attachment to the biochip, or may be directly synthesized on the biochip.

The solid substrate may be a material that may be modified to contain discrete individual sites appropriate for the attachment or association of the probes and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate may be planar, although other configurations of substrates may be used as well. For example, probes may be placed on the inside surface of a tube, for flow-through sample analysis to minimize sample volume. Similarly, the substrate may be flexible, such as flexible foam, including closed cell foams made of particular plastics.

The biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker. The probes may be attached to the solid support by either the 5' terminus, 3' terminus, or via an internal nucleotide.

The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography.

9. miRNA Expression Analysis

A method of identifying miRNAs that are associated with disease or a pathological condition, such as viral infection is also provided, comprising contacting a biological sample with a probe or biochip provided herein and detecting the amount of hybridization. PCR may be used to amplify nucleic acids in the sample, which may provide higher sensitivity. A bioinformatic method may be used to identify a specific miRNA target or target pattern that is common among different viruses, and to identify a target of human miRNA in a viral genome. The method may be used in a system to identify a mRNA target of a host or viral miRNA. The target may be useful to evaluate the role of a miRNA in a virus-host interaction by up or down regulation, or for the development of a therapeutic use of a miRNA.

The level of the nucleic acid in the sample may also be compared to a control sample (e.g., a normal cell) to determine whether the nucleic acid is differentially expressed (e.g., overexpressed or underexpressed). The ability to identify miRNAs that are differentially expressed in pathological cells compared to a control can provide high-resolution, high-sensitivity datasets which may be used in the areas of diagnostics, prognostics, therapeutics, drug development, pharmacogenetics, biosensor development, and other related areas. An expression profile generated by the current methods may be a "fingerprint" of the state of the sample with respect to a number of miRNAs. While two states may have any particular miRNA similarly expressed, the evaluation of a number of miRNAs simultaneously allows the generation of a gene expression profile that is characteristic of the state of the cell. That is, normal tissue may be distinguished from diseased tissue. By comparing expression profiles of tissue in known different disease states, information regarding which miRNAs are associated in each of these states may be obtained. Then, diagnosis may be performed or confirmed to determine whether a tissue sample has the expression profile of normal or disease tissue. This may provide for molecular diagnosis of related conditions.

10. Determining Expression Levels

The expression level of a viral infection- or disease-associated nucleic acid may be informative in a number of ways. For example, differential expression of a viral infection- or disease-associated nucleic acid compared to a control may be diagnostic of a patient suffering from the viral infection or disease. Expression levels of a viral infection- or disease-associated nucleic acid may also be used to monitor the treatment and viral infection or disease state of a patient. Furthermore, expression levels of a viral infection- or disease-associated miRNA may allow the screening of drug candidates for altering a particular expression profile or suppressing an expression profile associated with viral infection or disease.

A target nucleic acid may be detected and levels of the target nucleic acid measured by contacting a sample comprising the target nucleic acid with a biochip comprising an attached probe sufficiently complementary to the target nucleic acid and detecting hybridization to the probe above control levels.

The target nucleic acid may also be detected by immobilizing the nucleic acid to be examined on a solid support such as nylon membranes and hybridizing a labeled probe with the sample. Similarly, the target nucleic may also be detected by immobilizing the labeled probe to a solid support and hybridizing a sample comprising a labeled target nucleic acid. Following washing to remove the non-specific hybridization, the label may be detected.

The target nucleic acid may also be detected in situ by contacting permeabilized cells or tissue samples with a labeled probe to allow hybridization with the target nucleic acid. Following washing to remove the non-specifically bound probe, the label may be detected.

These assays can be direct hybridization assays or can comprise sandwich assays, which include the use of multiple probes, as generally outlined in U.S. Pat. Nos. 5,681,702; 5,597,909; 5,545,730; 5,594,117; 5,591,584; 5,571,670; 5,580,731; 5,571,670; 5,591,584; 5,624,802; 5,635,352; 5,594,118; 5,359,100; 5,124,246; and 5,681,697, each of which is hereby incorporated by reference.

A variety of hybridization conditions may be used, including high, moderate and low stringency conditions as outlined above. The assays may be performed under stringency conditions which allow hybridization of the probe only to the target. Stringency can be controlled by altering a step parameter that is a thermodynamic variable, including, but not limited to, temperature, formamide concentration, salt concentration, chaotropic salt concentration pH, or organic solvent concentration.

Hybridization reactions may be accomplished in a variety of ways. Components of the reaction may be added simultaneously, or sequentially, in different orders. In addition, the reaction may include a variety of other reagents. These include salts, buffers, neutral proteins, e.g., albumin, detergents, etc. which may be used to facilitate optimal hybridization and detection, and/or reduce non-specific or background interactions. Reagents that otherwise improve the efficiency of the assay, such as protease inhibitors, nuclease inhibitors and anti-microbial agents may also be used as appropriate, depending on the sample preparation methods and purity of the target.

11. Diagnostic

A method of diagnosis is also provided. The method comprises detecting a differential expression level of a disease-associated nucleic acid in a biological sample. The sample may be derived from a patient. Diagnosis of a disease state in a patient may allow for prognosis and selection of therapeutic strategy. Further, the developmental stage of cells may be classified by determining temporarily expressed disease-associated nucleic acids.

In situ hybridization of labeled probes to tissue arrays may be performed. When comparing the fingerprints between an individual and a standard, the skilled artisan can make a diagnosis, a prognosis, or a prediction based on the findings. It is further understood that the genes which indicate the diagnosis may differ from those which indicate the prognosis and molecular profiling of the condition of the cells may lead to distinctions between responsive or refractory conditions or may be predictive of outcomes.

12. Drug Screening

A method of screening therapeutics is also provided. The method comprises contacting a pathological cell capable of expressing a disease related nucleic acid with a candidate therapeutic and evaluating the effect of a drug candidate on the expression profile of the disease associated nucleic acid. Having identified the differentially expressed nucleic acid, a variety of assays may be executed. Test compounds may be screened for the ability to modulate gene expression of the disease associated nucleic acid. Modulation includes both an increase and a decrease in gene expression.

The test compound or drug candidate may be any molecule, e.g., protein, oligopeptide, small organic molecule, polysaccharide, polynucleotide, etc., to be tested for the capacity to directly or indirectly alter the disease phenotype or the expression of the disease associated nucleic acid. Drug candidates encompass numerous chemical classes, such as small organic molecules having a molecular weight of more than 100 and less than about 500, 1,000, 1,500, 2,000 or 2,500 daltons. Candidate compounds may comprise functional groups necessary for structural interaction with proteins, particularly hydrogen bonding, and typically include at least an amine, carbonyl, hydroxyl or carboxyl group, preferably at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Combinatorial libraries of potential modulators may be screened for the ability to bind to the disease associated nucleic acid or to modulate the activity thereof. The combinatorial library may be a collection of diverse chemical compounds generated by either chemical synthesis or biological synthesis by combining a number of chemical building blocks such as reagents. Preparation and screening of combinatorial chemical libraries is well known to those of skill in the art. Such combinatorial chemical libraries include, but are not limited to, peptide libraries encoded peptides, benzodiazepines, diversomers such as hydantoins, benzodiazepines and dipeptide, vinylogous polypeptides, analogous organic syntheses of small compound libraries, oligocarbamates, and/or peptidyl phosphonates, nucleic acid libraries, peptide nucleic acid libraries, antibody libraries, carbohydrate libraries, and small organic molecule libraries.

13. Gene Silencing

Also provided is a method of reducing the expression of a target gene in a cell, tissue or organ. Expression of the target gene may be reduced by expressing a nucleic acid described herein that comprises a sequence substantially complementary to one or more binding sites of the target mRNA. The nucleic acid may be a miRNA or a variant thereof. The nucleic acid may also be pri-miRNA, pre-miRNA, or a variant thereof, which may be processed to yield a miRNA. The expressed miRNA may hybridize to a substantially complementary binding site on the target mRNA, which may lead to activation of RISC-mediated gene silencing. An example for a study employing over-expression of miRNA is provided in Yekta et al 2004, Science 304-594, which is incorporated herein by reference. The nucleic acids described herein may also be used to inhibit expression of target genes using antisense methods well known in the art, as well as RNAi methods described in U.S. Pat. Nos. 6,506,559 and 6,573,099, which are incorporated by reference.

The target gene may be a viral gene, the level of which may be reduced by expressing a viral or human miRNA. The target gene may also be a human gene that is expressed upon viral infection, the level of which may be reduced by expressing a viral or human miRNA. The target of gene silencing may be a protein that causes the silencing of a second protein. By repressing expression of the target gene, expression of the second protein may be increased. Examples for efficient suppression of miRNA expression are the studies by Esau et al 2004 JBC 275-52361; and Cheng et al 2005 Nucleic Acids Res. 33-1290, which is incorporated herein by reference.

14. Gene Enhancement

Also provided is a method of increasing the expression of a target gene in a cell, tissue or organ. Expression of the target gene may be increased by expressing a nucleic acid described herein that comprises a sequence substantially complementary to a pri-miRNA, pre-miRNA, miRNA or a variant thereof. The nucleic acid may be an anti-miRNA. The anti-miRNA may hybridize with a pri-miRNA, pre-miRNA or miRNA, thereby reducing its gene repression activity. Expression of the target gene may also be increased by expressing a nucleic acid described herein that is substantially complementary to a portion of the binding site in the target gene, such that binding of the nucleic acid to the binding site may prevent miRNA binding.

The target gene may be a viral gene, expression of which may reduce infectivity of the virus. The target gene may also be a human gene, expression of which may reduce infectivity of the virus or increase resistance or immunity to the viral infection.

15. Reducing viral replication

A method of reducing the amount of viral replication is provided, which may occur via gene silencing or gene enhancement using the nucleic aid as described herein. The nucleic acid may also be used to reduce the expression of a target gene in a cell such as a viral gene in a virus-infected cell. Expression of the viral or target gene may be reduced by expressing the nucleic acid, which may comprise a sequence substantially complementary to one or more binding sites of the target gene. The nucleic acid may be a miRNA or a variant thereof. The nucleic acid may also be a pri-miRNA, pre-miRNA, or a variant thereof, which may be processed to yield a miRNA. The expressed miRNA may hybridize to a substantially complementary binding site on the target mRNA, which may lead to interruption of the function of the gene. In the case of a viral target, replication of the virus may be inhibited, and the viral infection may be reduced or eliminated.

The target gene may be a viral gene, which may be reduced by expressing a viral or human miRNA. The target gene may also be a human gene that is expressed upon viral infection, which may be reduced by expressing a viral or human miRNA. The target of gene silencing may be a protein that causes the silencing of a second protein. By repressing expression of the target gene, expression of the second protein may be decreased.

16. Therapeutic

Also provided is a method of modulating a disease or disorder, which may be associated with a viral infection. In general, the nucleic acid described herein may be used as a modulator of the expression of a gene that is at least partially complementary to the nucleic acid. Further, a miRNA molecule may act as a target for a therapeutic screening procedure, e.g. inhibition or activation of a miRNA molecule might modulate a cellular differentiation process, e.g. apoptosis.

Furthermore, an existing miRNA molecule may be used as a starting material for the manufacture of a sequence-modified miRNA molecule, in order to modify the target-specificity thereof, e.g. an oncogene, a multidrug-resistance gene or another therapeutic target gene. Further, a miRNA molecule may be modified, so that it may be processed and then generated as double-stranded siRNA that may again be directed against a therapeutically relevant target. Furthermore, a miRNA molecule may be used for tissue reprogramming procedures, e.g. a differentiated cell line might be transformed by expression of a miRNA molecule into a different cell type or a stem cell.

17. Compositions

Also provided herein is a pharmaceutical composition, which may comprise a nucleic acid described herein and optionally a pharmaceutically acceptable carrier. The nucleic acid may be an active ingredient of the composition. The composition may be used for diagnostic or therapeutic applications. The administration of the pharmaceutical composition may be carried out by known methods, wherein a nucleic acid is introduced into a desired target cell in vitro or in vivo.

The composition may be formulated in combination with appropriate, pharmaceutically acceptable carriers or diluents, and can be formulated into preparations in solid, semi-solid, liquid or gaseous forms, such as tablets, capsules, powders, granules, ointments, solutions, suppositories, injections, inhalants and aerosols. As such, administration of the agents can be achieved in various ways, including oral, buccal, rectal, parenteral, intraperitoneal, intradermal, transdermal, intracheal, etc.

18. Nucleic Acid Delivery

The nucleic acid may be introduced to a cell, tissue or organ in a single- or double-stranded form or capable of being expressed by a synthetic gene using methods well known to those skilled in the art, including as described in U.S. Pat. No. 6,506,559 which is incorporated by reference.

Methods for the delivery of nucleic acid molecules are described in Akhtar et al., (Trends Cell Bio. 2, 139, 1992). WO 94/02595 describes general methods for delivery of RNA molecules. These protocols can be utilized for the delivery of virtually any nucleic acid molecule. Nucleic acid molecules can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to oral (tablet or pill form) and/or intrathecal delivery (Gold, 1997, Neuroscience, 76, 1153-1158). Other approaches include the use of various transport and carrier systems, for example, through the use of conjugates and biodegradable polymers. More detailed descriptions of nucleic acid delivery and administration are provided for example in WO93/23569, WO99/05094, and WO99/04819.

The nucleic acids can be introduced into tissues or host cells by any number of routes, including viral infection, microinjection, or fusion of vesicles. Jet injection may also be used for intra-muscular administration, as described by Furth et al. (Anal Biochem 115 205:365-368, 1992). The nucleic acids can be coated onto gold microparticles, and delivered intradermally by a particle bombardment device, or "gene gun" as described in the literature (see, for example, Tang et al. Nature 356:152-154, 1992), where gold microprojectiles are coated with the DNA, then bombarded into skin cells.

19. Kits

Also provided is a kit comprising a nucleic acid described herein together with any or all of the following: assay reagents, buffers, probes and/or primers, and sterile saline or another pharmaceutically acceptable emulsion and suspension base. In addition, the kit may include instructional materials containing directions (e.g., protocols) for the practice of the methods described herein.

20. Virus

The methods and nucleic acids described herein may be associated with any one of a number of different visuses, including HSV1, HSV2, RSV, EBV, Influenza A, HCV, HPV, HIV, HBV, and Vaccinia. Influenza virus infection is a major public health problem, causing millions of cases of severe illness and as many as 500,000 deaths each year worldwide (WHO report, 2004, A56/23). Influenza virus has A, B and C types, among which the type A can be further classified into many sub-types according to the variations in NA and HA genes. Thus far, there have been 15 HA subtypes and 9 NA subtypes and the different combinations between HA and NA subtypes can form many types of influenza A virus subtypes.

Although inactivated vaccines are 60-80% effective against the matched influenza strains, vaccination coverage is a problem worldwide. Moreover, this strategy provides no protection against unexpected strains. Currently, antiviral drugs are the best defense against these outbreaks, but they provide only partial protection (Nicholson, etc., Lancet, 355: 1845-1850, 2000), usually companied with some side effects, especially to the central nervous system (Wenzel, JAMA, 283:1057-1059, 2000).

Epstein Barr Virus (EBV), a large DNA virus of the Herpes family that infects normal human B cells, is the etiologic agent of infectious mononucleosis and is strongly associated with Burkitt's lymphoma and nasopharingal carcinoma.

Herpes simplex virus type-1 and 2 (HSV1 and HSV2) enter and reactivate from latency in sensory neurons, although the events governing these processes are little understood. During latency, only the latency-associated transcripts are produced.

21. Disease

The methods and nucleic acids described herein may be associated with any one of a number of different diseases, including Burkitt's lymphoma, nasopharingal carcinoma, ovarian carcinoma, cervical cancer, hepatitis, mononucleosis, influenza, genital herpes, encephalitis, and bronchiolitis.

EXAMPLES

Example 1

Prediction of MiRNAs

We surveyed a number of viral genomes for potential miRNA coding genes using three computational approaches similar to those described in U.S. Patent Application No. 60/522,459, Ser. Nos. 10/709,577 and 10/709,572, the contents of which are incorporated herein by reference, for predicting miRNAs. The predicted hairpins and potential miRNAs were scored by thermodynamic stability, as well as structural and contextual features. The algorithm was calibrated by using miRNAs in the Sanger Database which had been validated.

1. Viral Genome Screen

Table 1 and Table 8 list the SEQ ID NO for each predicted hairpin ("HID") of a particular viral genome ("V"; See also Table 7). Table 1 also lists the genomic location for each hairpin ("Hairpin_Loc"). The format for the genomic location is a concatenation of <strand><start position>. For viruses that have more than one chromosome or segment, such as Influenza A, the segment number is identified in column "C" (viruses with only one chromosome have a value of 1 in this column). The genetic location is based on the NCBI—Entrez Nucleotides database. The Entrez Nucleotides database is a collection of sequences from several sources, including GenBank, RefSeq, and PDB. Table 7 shows the accession number and the build (version) for each of the viral genomes used in this screen. Two viruses in Table 7 have multiple accession numbers because each segment (i.e., chromosome analog) of the virus' genomes had a different accession number. One of the viruses has no accession number.

Table 1 also lists the SEQ ID NO ("MID") for each predicted miRNA and miRNA*. Table 1 also lists the prediction score grade for each hairpin ("P") on a scale of 0-1 (1 means that the hairpin is the most reliable), as described in Hofacker et al., Monatshefte f. Chemie 125: 167-188, 1994. Table 1 also lists the p-value ("Pval") calculated out of background hairpins for the values of each P scores. All the p-values were significant, i.e., less than 0.05. If the Pval is indicated as 0.0, then the Pval is less than 0.0001. The p-values were calculated by comparing the palgrade of the tested hairpin to the palgrade of other sequences without pre-selection of hairpins.

Table 1 also lists whether the miRNAs were validated by expression analysis ("E") (Y=Yes, N=No), as detailed in Table 2. It should be noted that failure to sequence or detect expression of a miRNA does not necessarily mean that a miRNA does not exist. Such undetected miRNAs may be expressed in tissues other than those tested. In addition, such undetected miRNAs may be expressed in the test tissues, but at a difference stage or under different conditions compared to the experimental cells.

Table 1 also lists a genetic location cluster ("LC") for those hairpins that are within 1,000 nucleotides of each other of a particular virus. Each miRNA that has the same LC shares the same genetic cluster. Hairpins that overlap were not clustered.

Example 2

Prediction of Target Genes

The predicted miRNAs from the computational screen of Example 1 were used to predict human and viral target genes and their binding sites using computational approaches for predicting miRNAs, similar to approaches described in U.S. Patent Application No. 60/522,459, Ser. Nos. 10/709,577 and 10/709,572, the contents of which are incorporated herein by reference.

1. Human Genome Screen
   a. Human Target Genes

Table 3 and Table 9 list a predicted human target gene for each miRNA ("MID") from a particular virus ("V") and its hairpin ("HID") from the viral genome screen. The virus codes listed in "V" are, as for Table 1, defined in Table 7. The names of the target genes ("Target_Gene") in Table 3 were taken from NCBI Reference Sequence release 9 (http://www.ncbi.nlm.nih.gov; Pruitt et al., Nucleic Acids Res, 33(1): D501-D504, 2005; Pruitt et al., Trends Genet., 16(1):44-47, 2000; and Tatusova et al., Bioinformatics, 15(7-8):536-43, 1999). Target genes were identified by having a mammalian conserved perfect complementary match of a 7 nucleotide miRNA seed (positions 2-8) and an A on the UTR (total=8 nucleotides). For a discussion on identifying target genes, see Lewis et al., Cell, 120: 15-20, (2005). For a discussion of the seed being sufficient for binding of a miRNA to a UTR, see Lim Lau et al., (Nature 2005) and Brenneck et al, (PLoS Biol 2005).

The binding site screen only considered the first 4000 nucleotides per UTR and considered the longest transcript when there were several transcripts per gene. The filtering reduced the total number of transcripts from 23626 to 14239. Table 3 lists the SEQ ID NO for the predicted binding sites ("Binding_site") for each target gene. The sequence of the binding site includes the 20 nucleotides 5' and 3' of the binding site as they are located on the spliced mRNA. In cases that the binding site is comprised from 2 exons, 20 nucleotides are included from both 5' and 3' ends of both exons.

b. Viral Target Genes

Human Herpes virus 1 and 2 are related to any of several inflammatory diseases caused by a herpesvirus and marked in one case by groups of watery blisters on the skin or mucous membranes (as of the mouth and lips) above the waist and in the other by such blisters on the genitals. Human herpesvirus 4 (Epstein-Barr virus) is capable of causing infectious mononucleosis and is associated with Burkitt's lymphoma and nasopharyngeal carcinoma. HIV strains are related to Acquired Immune Deficiency Syndrome (AIDS). Hepatitis B and C viruses are capable of causing inflammation of the liver. Human papillomavirus is capable of causing cervical cancer, human respiratory syncytial virus (RSV) is capable of causing respiratory disease, and Influenza A virus is capable of causing Influenza. Vaccinia virus has not been shown to be capable of causing disease in humans, and is usually used for the preparation of vaccines.

Example 3

Validation of miRNAs

To confirm the hairpins and miRNAs predicted in Example 1, we detected expression in various tissues using the high-throughput microarrays similar to those described in U.S. Patent Application No. 60/522,459, Ser. Nos. 10/709,577 and 10/709,572, the contents of which are incorporated herein by reference. For each predicted precursor miRNA, mature miRNAs derived from both stems of the hairpin were tested.

1. Expression Analysis

Table 2 shows the hairpins ("HID") of the third prediction set that were validated by detecting expression of related miRNAs ("MID") from a particular virus ("V"), as well as a code for the tissue ("Tissue") in which expression was detected. In cases where there was more than one score from the same miRNA in the same tissue, only the miRNA with the higher score is presented.

The tissue and disease codes are listed in Table 4 and Table 5, respectively. Table 6 shows the relationship between each gene and at least one disease, enabling a miRNA described herein to be connected to a disease. Table 6 condenses data derived from OMIM and lists for each gene the numeric code(s) of the disease(s) associated with the gene.

All the tissues disclosed give an indication of a viral disease. The fact that significant expression of the virus was measured implies that in this tissue it may be involve in a viral disease(s). For example, if a miRNA from HIV is expressed in a T cell line it may have an effect on AIDS. Of course cell lines represent only subset of the features of a tissue as its function in an organ however we can deduce from the expression as it is measured in the cell line.

Table 2 also shows the chip expression score grade, which ranges from 500 to 65000 ("S"). A threshold of 500 was used to eliminate non-significant signals and the score was normalized by miRNA microarray probe signals from different experiments. Variations in the intensities of fluorescence material between experiments may be due to variability in RNA preparation or labeling efficiency. Normalization was performed based on the assumption that the total amount of miRNAs in each sample was relatively constant. First, the background signal was subtracted from the raw signal of each probe, where the background signal was defined as 400. Next, each miRNA probe signal was divided by the average signal of all miRNAs, multiplied by 10000 and added back the background signal of 400. Thus, by definition, the sum of all miRNA probe signals in each experiment was 10400.

Table 2 also shows a statistical analysis of the normalized signal ("Spval") calculated on the normalized score. For each miRNA, a relevant control group was used out of the full predicted miRNA list. Each miRNA had an internal control of probes with mismatches. The relevant control group contained probes with similar C and G percentage (abs diff<5%) in order to have a similar Tm. The probe signal P value is the ratio over the relevant control group probes with the same or higher signals. The results were p-value ≦0.05 and the score was above 500. In those cases for which the SPVal is listed as 0.0, the value is less than 0.0001.

2. Sequencing

To further validate the hairpins ("HID") of the second prediction, a number of miRNAs were validated by sequencing methods similar to those described in U.S. Patent Application No. 60/522,459, Ser. Nos. 10/709,577 and 10/709,572, the contents of which are incorporated herein by reference.

3. Northern Blot Analysis

Figure 6:
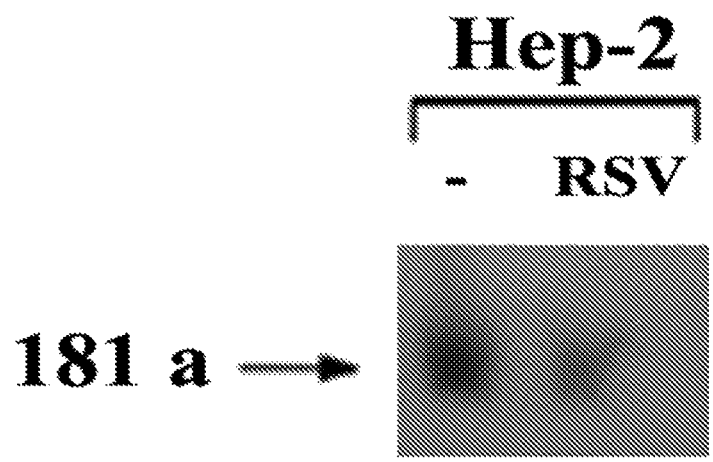
FIG. 6 shows Northern blot analysis of hsa-miR-181a (SEQ ID NO: 15,366) differentially expressed in HEp2 uninfected (−) and RSV infected cells.
Figure 9:
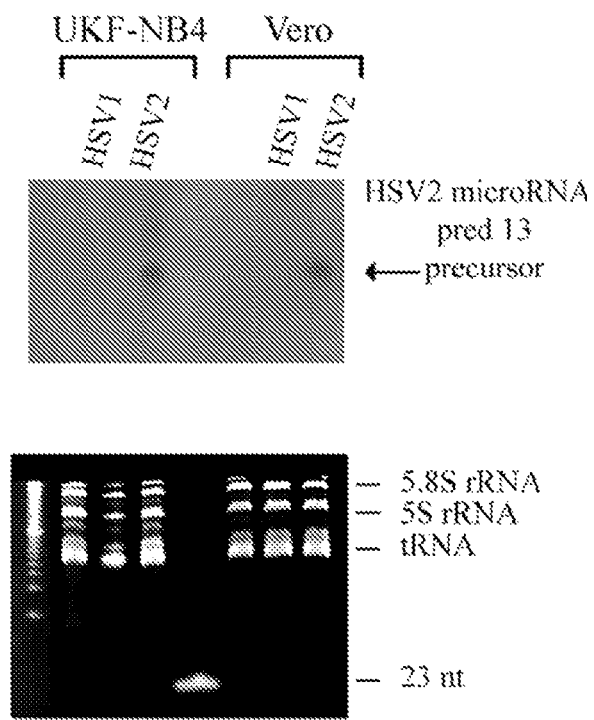
FIG. 9 shows Northern blot analysis of HSV2 microRNA-pred-13 (SEQ ID NO: 15,376). The lower part of the figure depicts Ethidium Bromide staining of the gel.
Figure 10:
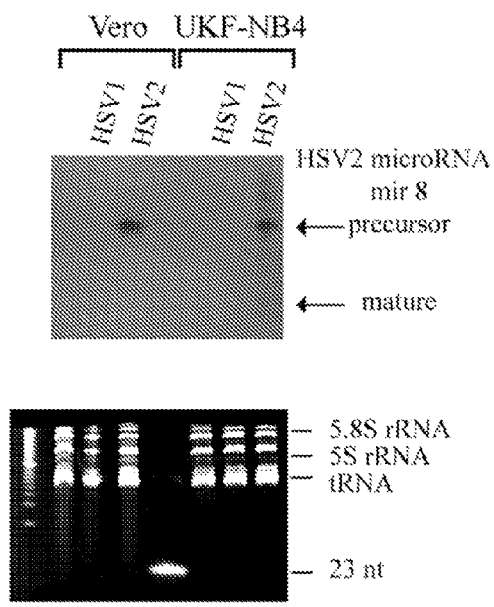
FIG. 10 shows Northern blot analysis of HSV2 microRNA-8 (SEQ ID NO: 15,377). The lower part of the figure depicts Ethidium Bromide staining of the gel.

A group of miRNAs were validated by Northern blot analysis, as shown in FIGS. 6, 9 and 10.

Example 4

Preparation of RNA Libraries from Virus-infected Cells and from Interferon α Treated Cells RNA libraries from virus-infected cells were prepared. For each library from infected cells, a control library from uninfected cells was also prepared. Total RNA was extracted from the paired cell lines (infected and uninfected) and labeled directly with either Cy5 or Cy3 (mirVana™ miRNA Labeling Kit, Ambion). Each set (labeled with either Cy3 or Cy5) was tested on the same micro-array slide of microRNAs (MIRDICATOR™, Rosetta Genomics).

RNA libraries were prepared from the following cell lines and viruses:
 a. Primary human fibroblasts (HF, from amnion synthesis), human neuroblastoma cell line (UKF NB4), and Vero cells, infected with HSV1 or HSV2, including libraries of early stage and late stage of infection for both viruses.
 b. HEp2 cells infected with Respiratory Syncytial Virus (RSV).
 c. MDCK cells (dog cells) infected with Influenza A (FluA).

In each case a library was also prepared from an uninfected control of the same cell line.

RNA libraries were also prepared from interferon α treated cells and from untreated cells to evaluate the effect of interferon α on microRNA production.

MIRDICATOR™ microRNA array were used to detect novel host and viral encoded miRNAs in the libraries (phase-1).

Glass slides were printed with probes of all the known hsa-mirs in anti-sense (AS) orientation; as well as various positive and negative controls (e.g. U6). In addition, AS probes to the predictions of microRNAs of viral genes were included. The predicted viral-microRNAs that were probed and analyzed were: HSV1, HSV2, RSV, and FluA microRNAs. Therefore, for single hybridization, two sets of positive signals on the microRNA array were obtained: expression of host (human) microRNAs and expression of viral microRNAs, in infected versus uninfected cells.

Example 5

Use of MIRDICATOR™ MicroRNA Array to Detect RSV Induced miRNAs

Total RNA was extracted from HEp2 cells infected with RSV or from control non-infected HEp2 cells and labeled with cy3 and cy5. The probes were hybridized together to the same microRNA array slide. The results depict signals for all microRNAs for both probes plotted against each other.

FIG. 1 shows the results of RSV infected and uninfected HEp2 cells hybridized on microRNA array. The human microRNA RG_AMB_10594 (SEQ ID NO: 15,374) was significantly upregulated in the RSV infected HEp2 cells as compared to uninfected control cells. The results suggest that host microRNAs may play a role in RSV replication.

Example 6

Use of MIRDICATOR™ to Detect FluA Encoded MicroRNAs

MDCK cells were infected with FluA and control cells were left uninfected. Three days after infection RNA was extracted, labeled with Cy3 and Cy5 and hybridized to the glass-microRNA array.

Figure 2A:
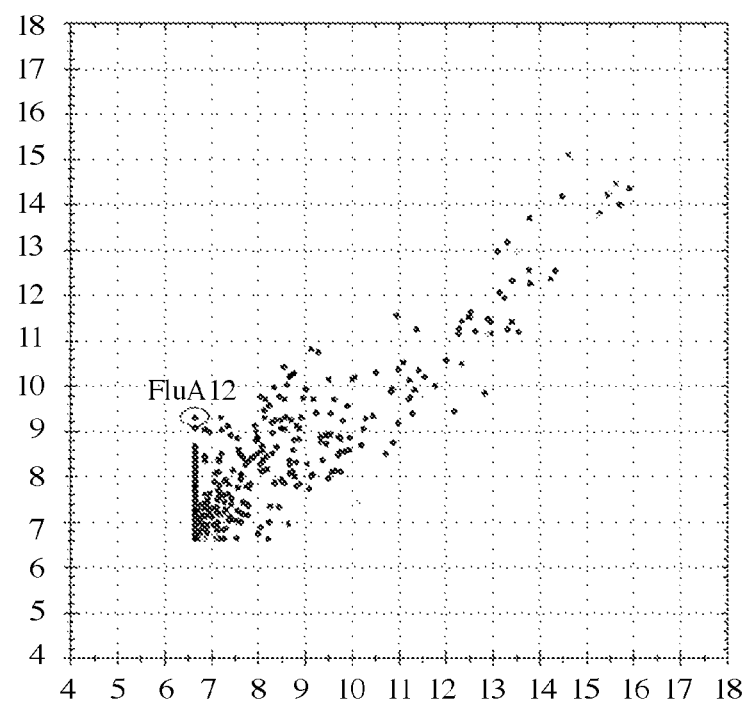
FIGS. 2A-2B show microRNA expression profiling of MDCK cells infected with Influenza A (FluA) as compared to uninfected control cells using miRdicator™ microRNA array. The expressed microRNA of FluA-12 (SEQ ID NO: 15,378) is circled. Two independent experiments are shown.
Figure 2B:
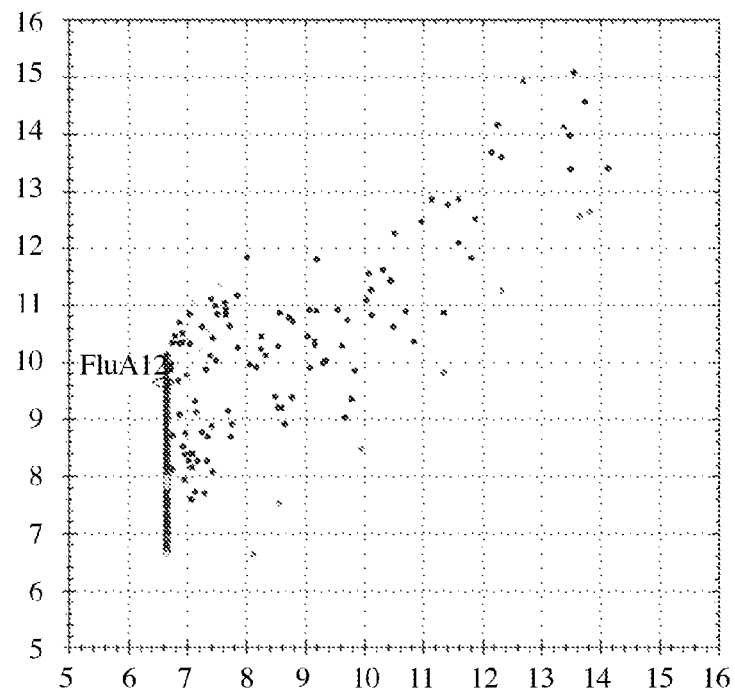

The results shown in FIGS. 2A-2B as a plot of MDCK cells infected with FluA vs. uninfected cells. Two independent experiments are shown. Out of 12 FluA probes (predicted by the bioinformatics-algorithm and spotted on the microRNA array), one, FluA-12 (SEQ ID NO: 15,378), gave a positive signal as shown circled in FIGS. 2A-2B. This viral-microRNA is validated by real time PCR for microRNAs (MIR-PCR, see details of the procedure below).

Example 7

Use of MIRDICATOR™ to detect HSV-1 & HSV-2 Encoded MicroRNAs

Neuroblastoma, Vero cells (cell line from green monkey's kidney) and human fibroblasts (HF) were infected with either HSV-1 or HSV-2. RNAs were extracted and labeled with cy3 and cy5. Eighteen samples from Vero cells and human fibroblasts (HF) were hybridized together to the same type of microRNA array slide. Each set of samples were either uninfected or infected with HSV-1 or with HSV-2. The results depict signals for all microRNAs from both probes, plotted against each other.

Figure 3:
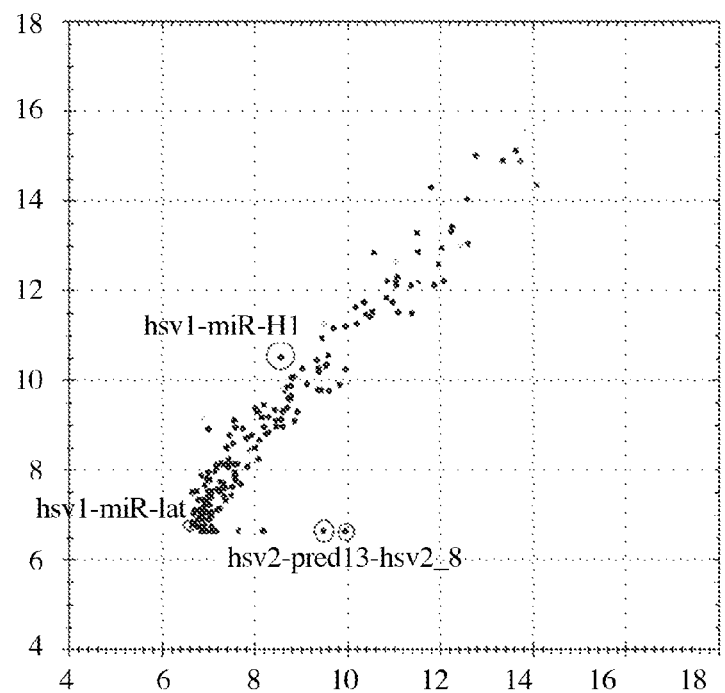
FIG. 3 shows microRNA expression profiling of herpes simplex virus type 1 (HSV1) microRNAs in Vero cells infected with HSV1 and HSV2 as compared to uninfected control cells. The expressed microRNA HSV1-miR-H1 (SEQ ID NO: 15,375) is indicated.

As shown in FIG. 3, the expression of hsvl-miR-H1 (SEQ ID NO: 15,375) was found in the late stage of HSV-1 infected Vero cells.

Figure 4:
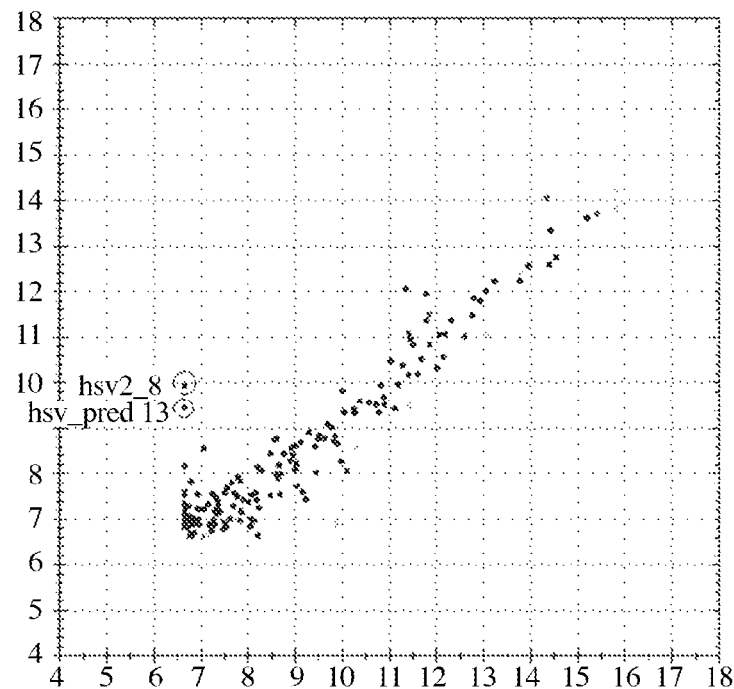
FIG. 4 shows microRNA expression profiling of HSV2 microRNAs in Vero cells infected with HSV2. The expressed microRNAs: HSV2-Pred13 (SEQ ID NO: 15,376) and HSV2-8 (SEQ ID NO: 15,377) are indicated.

Two novel microRNAs of HSV-2: hsv2-8 (SEQ ID NO: 15,377) and hsv2-pred13 (SEQ ID NO: 15,376) were found to be expressed in HSV2-infected Vero cells as shown in FIG. 4, and to a lesser extent in human neuroblastoma cell (UKF-NB4). These microRNAs are originated from the 3' arm and the 5' arm of the same pre-microRNA and are found twice in the HSV-2 genome. The HSV-2 microRNAs were found to be expressed at the late stage of infection. These are the first validated two microRNAs of HSV-2, a main cause of genital herpes. The data was confirmed further by MIR-PCR (FIG. 7) and by Northern blot analyses (FIGS. 9-10).

Example 8

Use of MicroRNA Array miRdicator™ to Detect Host MicroRNA Differential Expression During Viral Infections Up and down regulation of host microRNA (Homo sapiens, hsa-mirs) during viral infections could be observed in several infected cell lines. MDCK cells were infected with FluA. An uninfected control was included. Three days after infection RNA was extracted, labeled with Cy3 and Cy5 and hybridized to the glass-microRNA array.

Table 11 depicts differential expression of host microRNAs that are common to Homo sapiens and MDCK in FluA infected cells. The results are average of two experiments. These results are further validated by miRNA-RT-PCR and Northern blots.

Host hsa-miR-181a expression (SEQ ID NO: 15,366), is reduced not only in FluA infected MDCK cells, but also in RSV infected HEp2 cells (see Northern blot analysis in FIG. 6). The results of the microRNA array for hsa-miR-296 (SEQ ID NO: 15,370), hsa-miR-210 (SEQ ID NO: 15,372), hsa-miR-193a (SEQ ID NO: 15,367), hsa-miR-181a, hsa-miR-107 (SEQ ID NO: 15,368) and hsa-miR-103 (SEQ ID NO: 15,369) by Northern blot and miR-PCR analysis are under validation.

TABLE 11

Differential expression of host miRs in MDCK cells infected with FluA

| probe source | Signal from infected cells | Signal from un-infected cells | Fold change | comments |
|---|---|---|---|---|
| hsa_miR_296 | 2674.5 | 435.5 | (+)6 | up-regulated in infected cells |
| hsa_miR_210 | 461 | 1746 | (−)3.8 | down-regulated in infected cells |
| hsa_miR_193a | 2116.5 | 11879 | (−)5.6 | down-regulated in infected cells |
| hsa_miR_181a | 1880.5 | 10124 | (−)5.4 | down-regulated in infected cells |
| hsa_miR_107 | 1160 | 6898 | (−)5.9 | down-regulated in infected cells |
| hsa_miR_103 | 661 | 4243 | (−)6.4 | down-regulated in infected cells |

Example 9

Higher Expression of Human hsa-miR-21 in Vero Cells Infected with HSV1 in Comparison to Vero Cells Infected with HSV2

Figure 8:
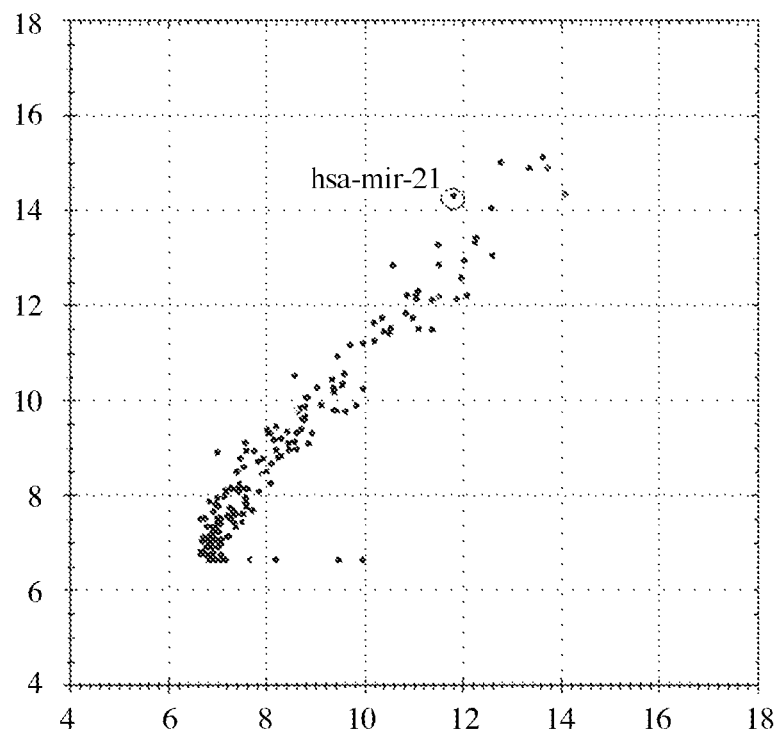
FIG. 8 shows higher expression of hsa-mir-21 (SEQ ID NO: 15,373) in Vero cells infected with HSV1 in comparison with HSV2 infected cells.

Following infection of Vero cells with HSV-1 and HSV-2, RNA was extracted, labeled with Cy3 and Cy5 and hybridized to the glass-microRNA array. As demonstrated in FIG. 8, hsa-miR-21 (SEQ ID NO: 15,373) is expressed at higher levels in Vero cells infected with HSV-1 in comparison to Vero cells infected with HSV2.

Example 10

Figure 5A:
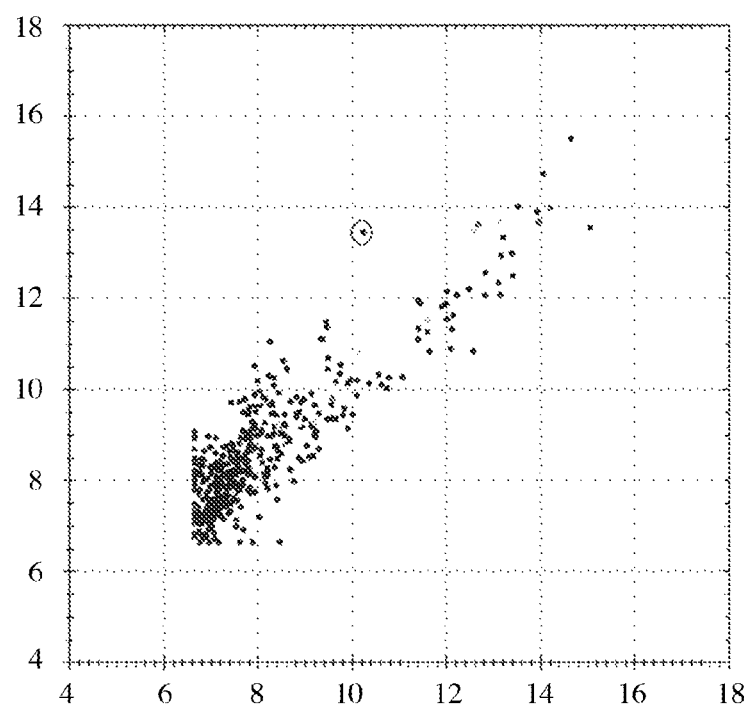
FIGS. 5A-5B show up-regulation of host microRNA AMB-10594 (SEQ ID NO: 15,374) (circled) following various viral infections of various cells: RSV infected HEp2 cells (FIG. 5A), HSV2 infected HF cells (FIG. 5B), HSV1 infected HF cells (FIG. 5D), and following interferon treatment of HF cells (FIG. 5C).
Figure 5B:
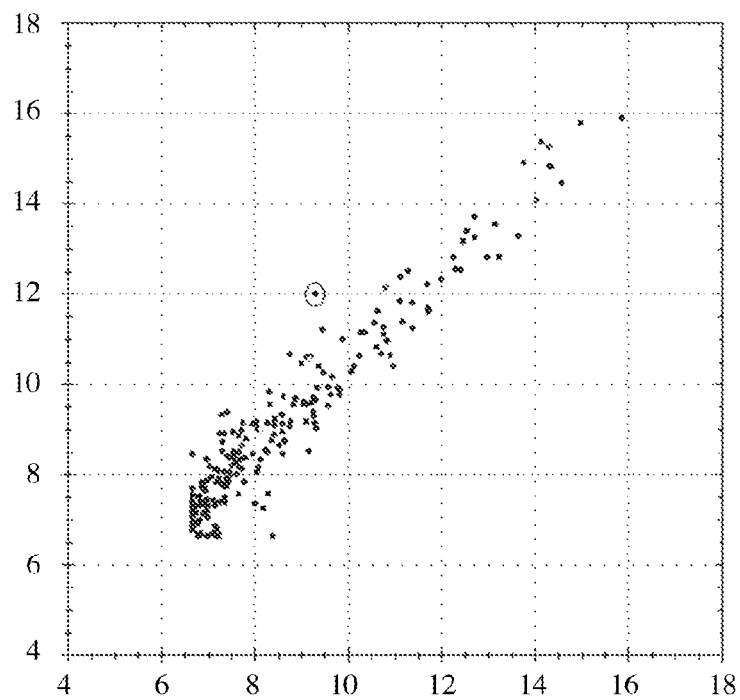
Figure 5C:
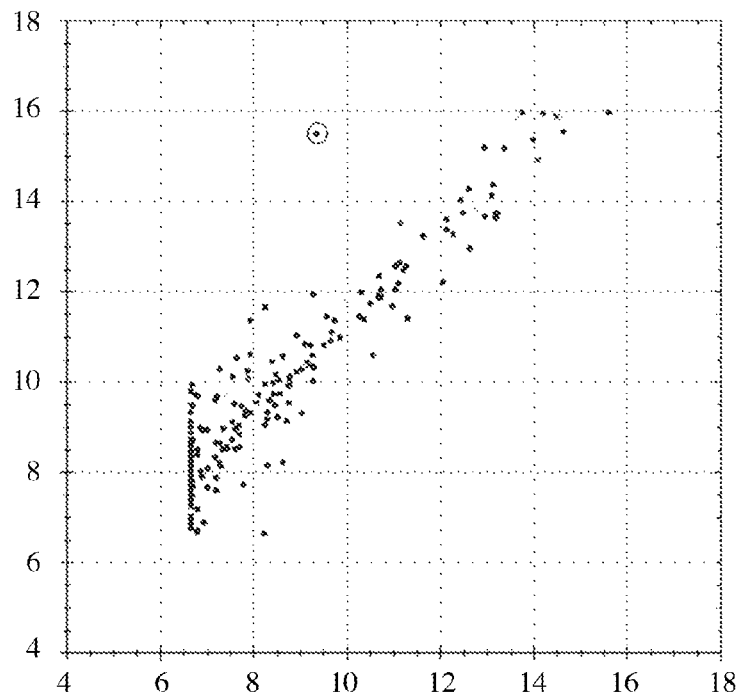
Figure 5D:
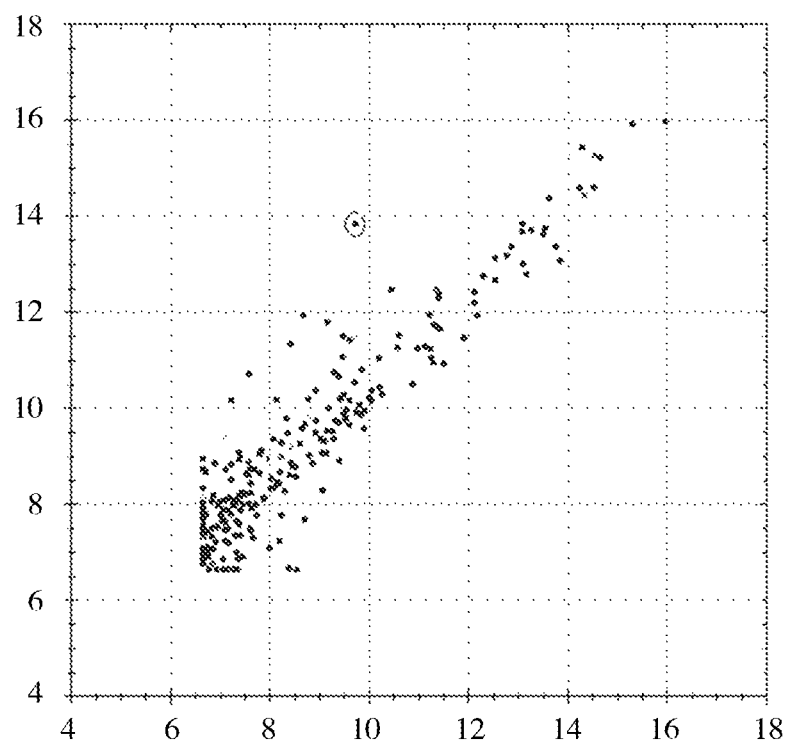

Expression of Host miRNA AMB-10594 in Viral Infected or Interferon Treated Cells The following tests were carried out: interferon α treated human fibroblasts (HF), HSV-1 and HSV-2 infected HF cells, and RSV infected Hep2 cells. All tests included an untreated or uninfected control. Three days after interferon α treatment or viral infection RNA was extracted, labeled with Cy3 and Cy5 and hybridized to the glass-microRNA array. As shown in FIG. 5, increased expression of host-miR AMB-10594 (SEQ ID NO: 15,374) (shown circled) was found in: interferon treated HF cells (FIG. 5C), HSV1 infected HF cells (FIG. 5D), HSV2 infected HF cells (FIG. 5B), and RSV infected HEp2 cells (FIG. 5A). In each of the graphs the treated/infected cells are plotted against the untreated/uninfected cells.

Example 11

Validation of the Results of the Microarray Screening by Northern Blot Analysis and by Cloning of miRNAs from Libraries of Virus Infected and Cytokines Treated Cells The results obtained from the microarray analysis were validated in two procedures:

I. Northern blot analysis. Northern blot analysis comparing RSV infected HEp2 cells with uninfected HEp2 cells was performed. 50 ug of RNA/slot were subjected to acrylamide-gel electrophoresis. Northern blot analysis was performed using a $P^{32}$-labeled-AS-probe to human hsa-miR-181a. The result shown in FIG. 6 indicates the down-regulation of the host miR in the RSV infected cells, thus confirming the microarray results.

II. Real time PCR, aimed at amplification of miRs (miR-PCR), adopted from Shi and Chiang, (Biotechniques, 2005. 39(4): p. 519-25). As little as 100 pg total RNA is polyadenylated and reverse-transcribed with a poly(T) adapter into cDNAs for real-time PCR using the miR-specific forward primer and the sequence complementary to the poly(T) adapter as the reverse primer. This real-time PCR method is simple and sensitive for quantifying the expression of miRs and also reveals miR tissue-specific expression patterns that cannot be resolved by Northern blot analysis.

Figure 7A:
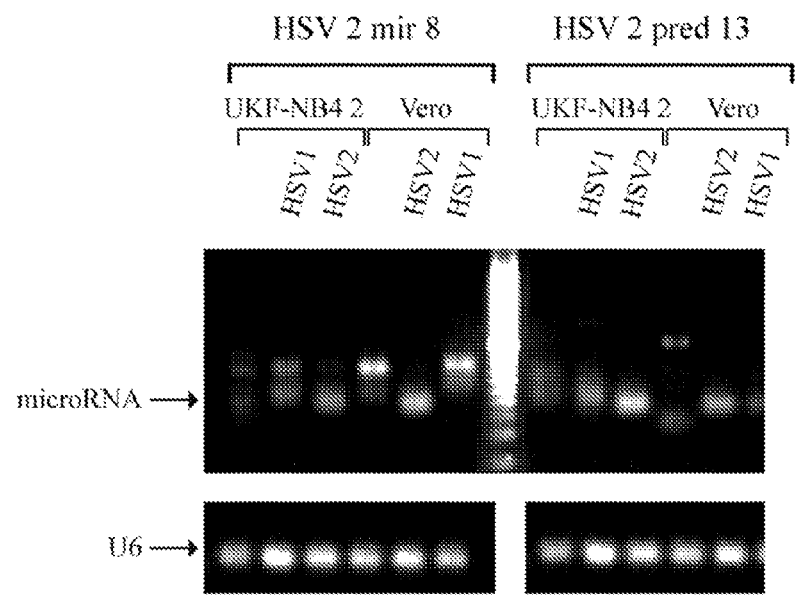
FIGS. 7A-7B show real time PCR analysis of HSV2 microRNA-pred-13 (SEQ ID NO: 15,376), HSV2 microRNA-8 (SEQ ID NO: 15,377) and their bulge.
Figure 7B:
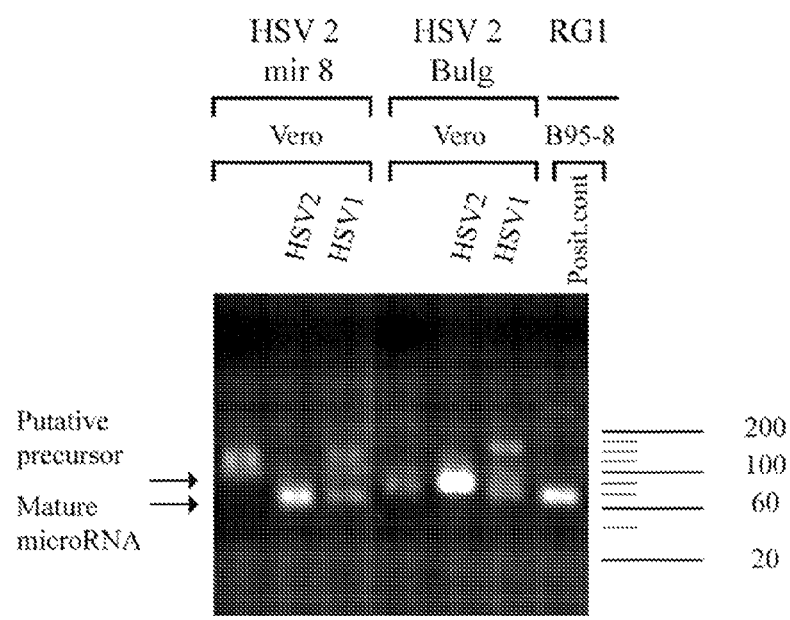

Analysis by miR-PCR demonstrated specific expression of the two novel HSV2 miRs (HSV2-miR-8 (SEQ ID NO: 15,377) and HSV2-mir-pred13 (SEQ ID NO: 15,376) in HSV2 infected neuroblastoma (UKF-NB4) and Vero cells. Total RNA was extracted from infected cells, polyadenylated and reverse-transcribed with a poly(T) adapter into cDNAs. The results are shown in FIG. 7: miR-specific forward primer HSV2-miR-8 (FIGS. 7A and 7B), HSV2-miR-pred13 (FIG. 7A) or bulge-primer (FIG. 7B). The reverse primer used was the sequence complementary to the poly(T) adapter. The products were subjected to agarose gel electrophoresis to determine their relative size. Nonspecific bands formed the same pattern in uninfected and HSV1 infected cells.

The results of the miR-PCR revealed a bulge probe (as expected), a higher band of about 100 nucleotides corresponding to the pre-microRNA precursor of these miRs (FIG. 7).

For Northern blot analysis, total RNA was extracted from either Vero cells or human neuroblastoma cells (UKF-NB4): uninfected, and HSV-1 and HSV-2 infected. The samples were enriched for small RNAs (Ambion kit). The small RNAs samples were run on Urea gel, 10 μg/lane, blotted to Nitrocellulose and hybridized with $^{32}P$ labeled probe to HSV2-mir-pred-13 or with $^{32}P$ labeled probe to HSV2-mir-8 (SEQ ID NO: 15,377). As shown in FIG. 9, after exposure of 30 days the precursor (~100 nts) of HSV2-mir-pred-13 (15,376) was visible. As shown in FIG. 10, the precursor of HSV2-mir-8 (~100nts) was visible and in UKF-NB4, a band at the region of ~22nts was also detected. The hybridization was specific to HSV2; no signal was detected under the same conditions with either uninfected cells or cell infected with HSV1. Experiments with specific inhibitors to these HSV2 miRs will help to determine their role in HSV-2 infection.

Example 12

Epstain Barr-Virus (EBV) MicroRNAs are Differentially Expressed and can Block the Viral Replication The EBV virus encodes several distinct miRNAs in latently infected cells that are located in two main clusters. The BART miRNAs (SEQ ID NOs: 15,516, 15,520, 15,522, 15,524 and 15,526) are expressed at high levels in stages I and II of latency, whereas the BHRF1 miRNAs (e.g. SEQ ID NO: 15,518) are expressed at high levels in stage III latency, while being essentially undetectable in other stages of virus life cycle. Induction of lytic EBV replication in B95-8 cells, by Cisplatin and 12-O-tetradecanonoyl phorbol-13-acetate (TPA) with n-Butyric acid or by TET ON/OFF regulated expression of immediate early (IE) gene ZEBRA (BZLF1), resulted in high expression of one of the BHRF-1-microRNA-cluster. This cluster is localized on the 5' and 3'-UTRs of BHRF1 mRNA. ZEBRA, is IE key gene in EBV switch to lytic infection. EBV replication resulted in LMP-1 (latency associated protein 1) reduction and increased viral load as determined by FACS and RT-PCR.

B95-8 cells persistently infected with EBV were transfected with various antagonists (2-O-Methyl antimir oligonucleotides, SEQ ID NOs: 15,517, 15,519, 15,521, 15,523, 15,525, and 15,527) to EBV microRNAs. After 120 hrs, cells were harvested, DNA was extracted, and EBV DNA copies/ml was determined by qRTPCR, using commercial standards for EBV viral load (FIG. 11).

BHRF-1, a viral homologue to Bc12 oncogene, is also a member of the IE proteins of EBV. Antisense blockage of BHRF1-miRNA expression resulted in increased number of viral particles, up to ten fold, in comparison to GFP control nonspecific antisense treatment (FIG. 11).

Figure 11:
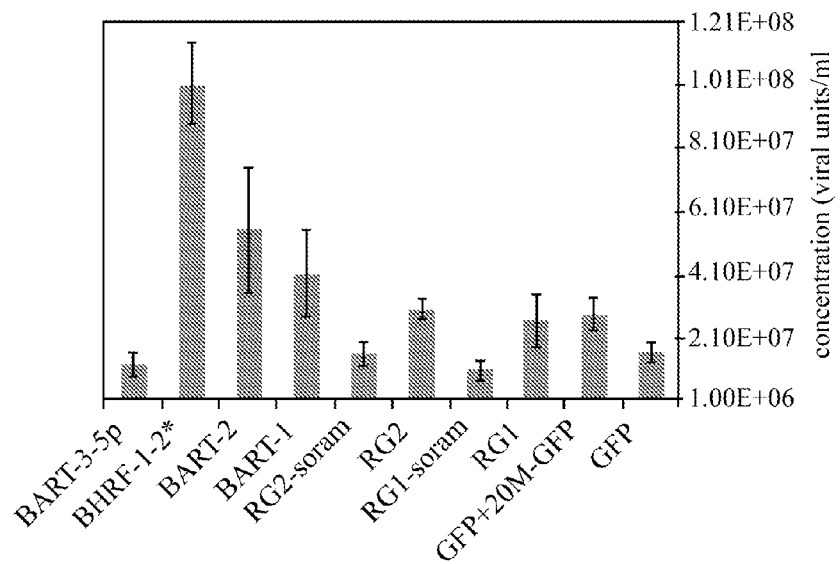
FIG. 11 shows the results of quantitative RT-PCR of EBV viral load in B95-8 cells transfected with EBV anti-mir oligonucleotides. B95-8 cells persistently infected with EBV were transfected with various antagonists (2-O-Methyl anti-mir oligonucleotides, SEQ ID NOs: 15,517, 15,519, 15,521, 15,523, 15,525, and 15,527) to EBV microRNAs. After 120 hrs, cells were harvested, DNA was extracted, and EBV DNA copies/ml was determined by qRTPCR, using commercial standards for EBV viral load.

Anti-microRNA to BART-2 had a moderate effect on viral replication (FIG. 11). Taken together, the result supports the notion that microRNAs play a central role in the control of viral life cycle and that their suppression leads to lytic activation and escape from latency. These findings also indicate the potential use of microRNAs as bases for antiviral therapies.

Over expression of BHRF1-miRNA is achieved by transfection of oligonucleotide mimicking the BHRF-1 microRNA into B-95-8 cells, using serial dilutions. The oligonucleotides are comprised of two small synthetic RNA molecules with 5'-phophorylation (5'-/phos/rUrArUrCrUrU-rUrUrGrCrGrGrCrArGrArArArUrUrGrA-3' (SEQ ID NO: 4,581); and 5'-/phos/rArArArUrUrCrUrGrUrUrGrCrAr-GrCrArGrArUrArGrC) (SEQ ID NO: 15,518), hybridized to each other Immediately after transfection and at 24 hrs intervals the transfected cells are harvested and EBV viral load is tested by RT-PCR.

Differential expression of EBV-mir-BHRF 1-2* (SEQ ID NO: 15,518) is tested in B-95-8, before and after induction with doxycycline treatment which initiates viral early cycles. RNA is extracted from the treated and untreated cells for Northern blot analysis.

Example 13

Testing the Effect of HSV2 MicroRNAs on HSV2 Replication

Neuroblastoma and Vero cells that are stably transfected with a plasmid containing the preMicrRNA of HSV2 (the precursor of HSV2-mir 8 and HSV2-mir-pred13, SEQ ID NOs: 15,389 and 15,392), cloned under IE-CMV-promoter in pEGFP-N1, Clontech), are infected with either HSV1 or HSV2 to test the specific effect of over expression of these two HSV2 microRNAs on HSV2 replication. Cells transfected with pEGFP-N1 empty vector and cells transfected with a vector containing the premicroRNA in AS-orientation are used as negative controls. Northern blot analysis is carried out to confirm that the construct produces the desired HSV-2-mirs and viral load is tested by RT-PCR to evaluate the effect of over expression of HSV-microRNAs on viral replication.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08481506B2). An electronic copy of the "Sequence Listing" will also be available from the USPTO upon request and payment of the fee set forth in 37 CFR 1.19(b)(3).

The invention claimed is:

1. A method of reducing the amount of virus replication in a target cell, the method comprising introducing into a target cell infected with the virus an effective amount of a composition comprising an isolated nucleic acid, wherein the nucleic acid consists of:

(a) SEQ ID NO: 15,372;

(b) a DNA encoding (a), wherein the DNA is identical in length to (a);

(c) a sequence at least 80% identical to (a) or (b), wherein the sequence is 13-33 nucleotides in length; and (d) the complement of any one of (a)-(c), wherein the complement is identical in length to (a).

2. The method of claim 1, wherein the target cell is in vitro.

3. The method of claim 1, wherein the target cell is in vivo.

4. The method of claim 1, wherein a subject comprises the target cell.

5. The method of claim 1, wherein the virus is hepatitis B virus.

6. A method of reducing the amount of virus replication in a target cell, the method comprising introducing into a target cell infected with the virus an effective amount of a composition comprising an isolated nucleic acid, wherein the nucleic acid consists of:
- (a) SEQ ID NO: 15,385;
- (b) a DNA encoding (a), wherein the DNA is identical in length to (a);
- (c) a sequence at least 80% identical to (a) or (b), wherein the sequence is 45-200 nucleotides in length; and
- (d) the complement of any one of (a)-(c), wherein the complement is identical in length to (a).

7. The method of claim 6, wherein the target cell is in vitro.

8. The method of claim 6, wherein the target cell is in vivo.

9. The method of claim 6, wherein a subject comprises the target cell.

10. The method of claim 6, wherein the virus is hepatitis B virus.

* * * * *